United States Patent
Butler et al.

(10) Patent No.: US 6,254,534 B1
(45) Date of Patent: Jul. 3, 2001

(54) RETRACTOR

(75) Inventors: John Butler; Derek William Young, both of Blackrock; Aoibheann Gill, Lanesboro; Alan Reid, Dublin; Frank Bonadio, Bray, all of (IE)

(73) Assignee: Atropos Limited, Co Wicklow (IE)

( * ) Notice: Subject to any disclaimer, the term of this patent is extended or adjusted under 35 U.S.C. 154(b) by 0 days.

(21) Appl. No.: 09/688,138

(22) Filed: Oct. 16, 2000

(30) Foreign Application Priority Data

| Oct. 14, 1999 | (IE) | 0861 |
| Dec. 16, 1999 | (IE) | 1053 |
| Feb. 18, 2000 | (EP) | 00650010 |

(51) Int. Cl.[7] .................................................. A61B 17/02
(52) U.S. Cl. ................................ 600/208; 600/206
(58) Field of Search .................................. 600/208, 206, 600/207, 236

(56) References Cited

U.S. PATENT DOCUMENTS

| 1,157,202 | * | 10/1915 | McLeland | 600/208 |
| 5,159,921 | * | 11/1992 | Hoover | 600/205 |
| 5,213,114 | * | 5/1993 | Bailey, Jr. | 600/208 |
| 5,366,478 |   | 11/1994 | Brinkerhoff et al. | |
| 5,514,133 |   | 5/1996 | Golub et al. | |
| 5,524,644 |   | 6/1996 | Crook . | |
| 5,649,550 |   | 7/1997 | Crook . | |
| 5,810,721 | * | 9/1998 | Mueller et al. | 600/206 |
| 5,906,577 | * | 5/1999 | Beane et al. | 600/208 |
| 6,033,426 | * | 3/2000 | Kaji | 600/207 |
| 6,142,935 | * | 11/2000 | Flom et al. | 600/206 |
| 6,142,936 | * | 11/2000 | Beane et al. | 600/208 |

FOREIGN PATENT DOCUMENTS

WO 98/48724    11/1998   (WO) .

* cited by examiner

Primary Examiner—Paul J. Hirsch
(74) Attorney, Agent, or Firm—Finnegan, Henderson, Farabow, Garrett, & Dunner, L.L.P.

(57) ABSTRACT

A retractor (101) for retracting the margins of a wound opening (103) comprises an inner anchoring O-ring (105) attached to a cylindrical sleeve (106) at a distal end and a reinforcing O-ring (109) attached to a proximal end of the sleeve (106). The sleeve (106) is led between an inner ring part (110) and a corresponding recess (116) in an outer ring part (111). The outer ring part (111) has anchor formations (120) over which the proximal end of the sleeve (106) is attached to anchor the sleeve (106). To retract the wound opening (103) the sleeve (106) is pulled while the guide rings (110, 111) are moved against the tissue surrounding the wound opening (103). This pulls the inner O-ring (105) against the inside of the tissue adjacent the wound opening (103), and retracts the wound opening (103). The sleeve (106) is manipulated locally for maximum retraction efficiency.

27 Claims, 24 Drawing Sheets

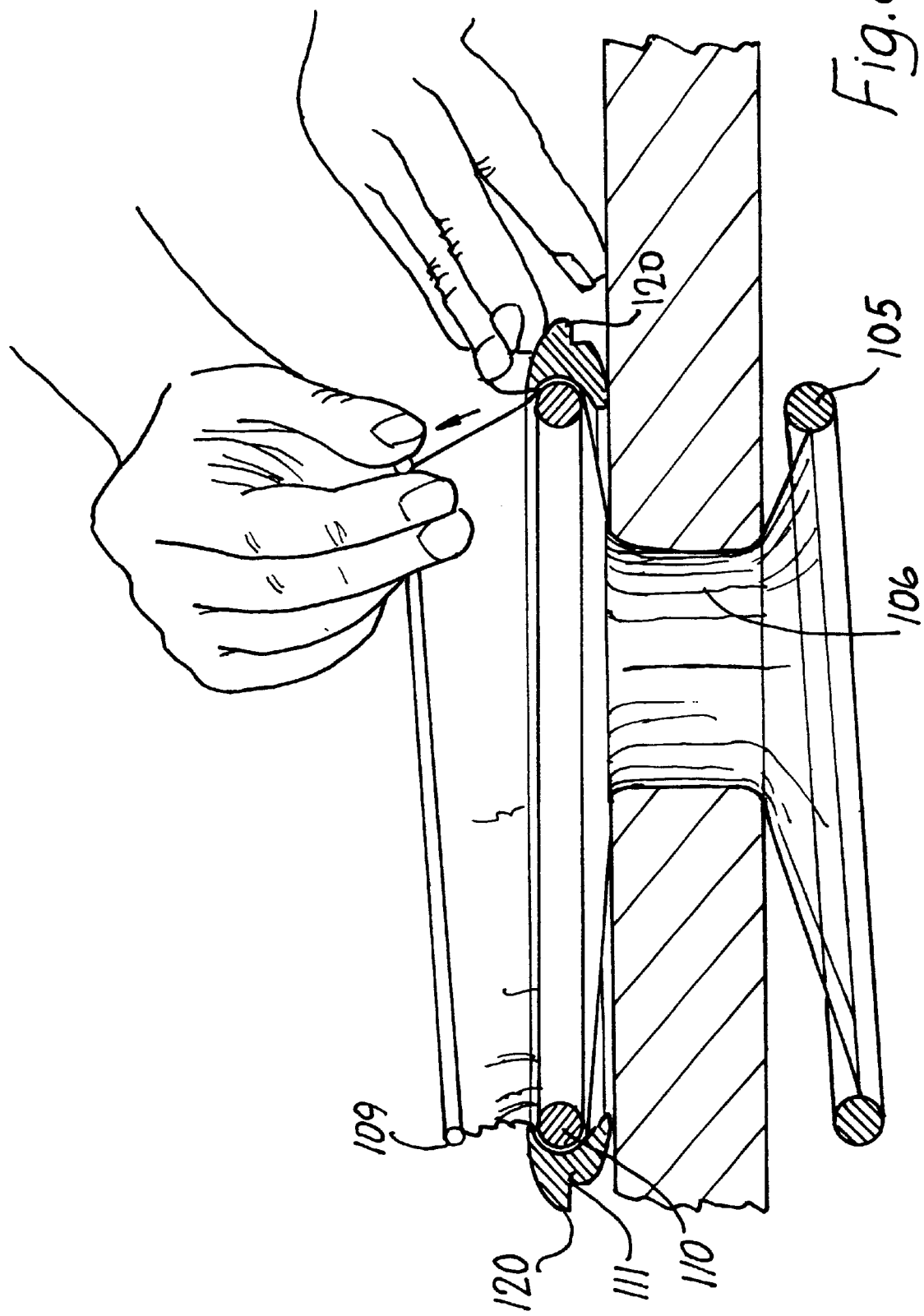

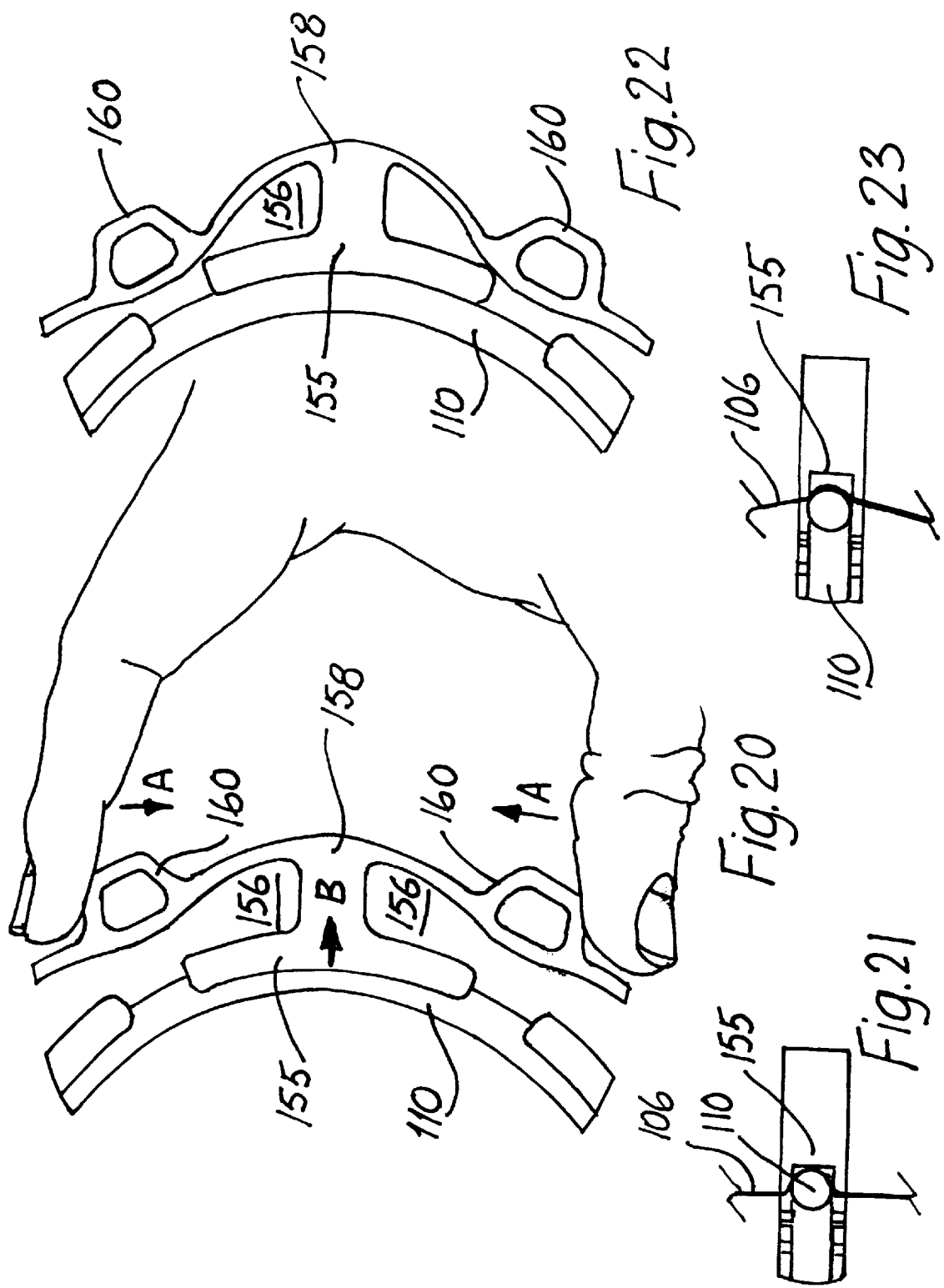

RETRACTOR

INTRODUCTION

The invention relates to a retractor. In particular the invention relates to a retractor for retracting the margins of an incision or a natural bodily orifice to provide maximum exposure of an organ or body structures for examination and/or access for surgical procedures, while also providing protection for the exposed sides of the incised tissue.

Various retractors are known. However in general known retractors are difficult and cumbersome to use, and/or are relatively expensive. In addition known retractors are limited to use with a particular size of incision and a particular patient anatomy.

This invention is directed towards providing an improved wound retractor which will overcome at least some of these problems, and in addition provide a means of wound protection during a surgical procedure.

STATEMENTS OF INVENTION

According to the invention there is provided a surgical wound retractor comprising:

- a distal anchoring member for insertion into a wound opening;
- a connecting means having an inner wound engaging portion and an outer portion, the wound engaging portion being mounted to the distal anchoring member, the connecting means having an insertion configuration in which the inner wound engaging portion has a reduced radial dimension and a retracting configuration;
- an external guide means for the outer portion of the connecting means;
- the external guide means being movable relative to the connecting means to shorten the axial extent of the connecting means and thereby bias the wound engaging portion of the connecting member into the retracting configuration to retract the wound opening laterally; and
- external anchoring means for anchoring the connecting means to maintain retraction of the opening.

In one preferred embodiment of the invention at least the inner wound engaging portion of the connecting means comprises a sleeve for extending around the wound opening to protect the opening.

In one embodiment the outer portion of the connecting means comprises a sleeve extension of the inner wound engaging portion of the connecting means.

Preferably the connecting means comprises a generally cylindrical sleeve.

In a preferred embodiment the guide means comprises an annular ring means. The annular ring means preferably comprises inner and outer ring parts between which the connecting means is led. In a preferred embodiment the outer ring part includes the anchor means for anchoring the connecting means. In one arrangement the anchor means comprises anchor formations on the outer ring to which the connecting means is attached on retraction of the opening.

Preferably the inner ring means defines a projection for location in a complementary recess of the outer ring with the connecting means located therebetween.

In one embodiment the inner ring is a relatively loose fit in the recess of the outer ring part.

Preferably at least portion of one of the ring parts is movable from a rest position in which the connecting member is substantially clamped between the ring parts to a release position in which at least portion of the connecting member is movable relative to the ring parts. Ideally only portion of the connecting member is movable relative to the ring parts in the release position.

In another embodiment the inner ring is a relatively tight fit in the outer ring part to grip the connecting member therebetween.

In one aspect of the invention the outer ring part comprises a plurality of interconnected segment which are independently movable to facilitate localised release of the connecting member for adjusting of the retraction force applied at the opening. The ring part or segment thereof is preferably manually manipulable between the clamped rest position and the release position.

In one embodiment of the invention the connecting means includes a proximal reinforcing means for engagement with the external anchoring means. Ideally the proximal reinforcing means is a proximal ring.

Preferably the distal anchoring means is of resilient material. Typically the distal anchoring means is an O-ring.

Preferably at least an outer surface of the guide means which engages with the connecting means is of a material with a low coefficient of friction such as polytetrafluroethylene.

In a particularly preferred embodiment the retractor includes a platform for attachment of another device to the retractor.

In an especially preferred arrangement one of the ring parts defines a platform for attachment of another device to the retractor.

In another aspect the invention provides a method for retracting a wound opening using a surgical wound retractor comprising a distal anchoring member, a connecting means having a wound engaging portion mounted to the distal anchoring member and an outer portion, an external guide means for the outer portion of the connecting means and an external anchoring means; the method comprising the steps:

- positioning the distal anchoring member to be retained inside a wound opening with the connecting means extending outwardly therefrom through the opening;
- moving the external guide means relative to the outer portion of the connecting means to shorten the axial extent of the connecting means and thereby bias the wound engaging portion into a retracting configuration to retract the wound opening; and
- anchoring the connecting means to maintain retraction of the wound opening.

Preferably the method includes the steps of moving the external guide means relative to the outer portion of the connecting means to partially retract the wound opening, gripping the outer portion of the connecting means and pulling it relative to the guide means to fully retract the wound opening.

In one embodiment the method includes the steps of:

(a) gripping a local section of the outer portion of the connecting means while the remaining section of the outer portion of the connecting means is anchored, (b) pulling the local section to increase the retraction at a local area of the wound opening, and (c) anchoring the local section of the connecting means.

Ideally the method includes repeating steps (a) to (c) for other local sections of the outer portion of the connecting means.

BRIEF DESCRIPTION OF THE DRAWINGS

The invention will be more clearly understood from the following description thereof given by way of example only with reference to the accompanying drawings, in which:

FIGS. 8(a) and 8(b) are side cross sectional views illustrating lateral retraction of the wound opening using the retractor of FIG. 2;

FIG. 20 is a schematic plan view illustrating manipulation of a part of the retractor of FIGS. 17 to 19;

FIG. 21 is a side cross sectional view of the retractor part in the configuration of FIG. 20;

FIG. 22 is a schematic plan view of the retractor part in a release position;

FIG. 23 is a side cross sectional view of the retractor part in the configuration of FIG. 22;

DETAILED DESCRIPTION

Figure 3:
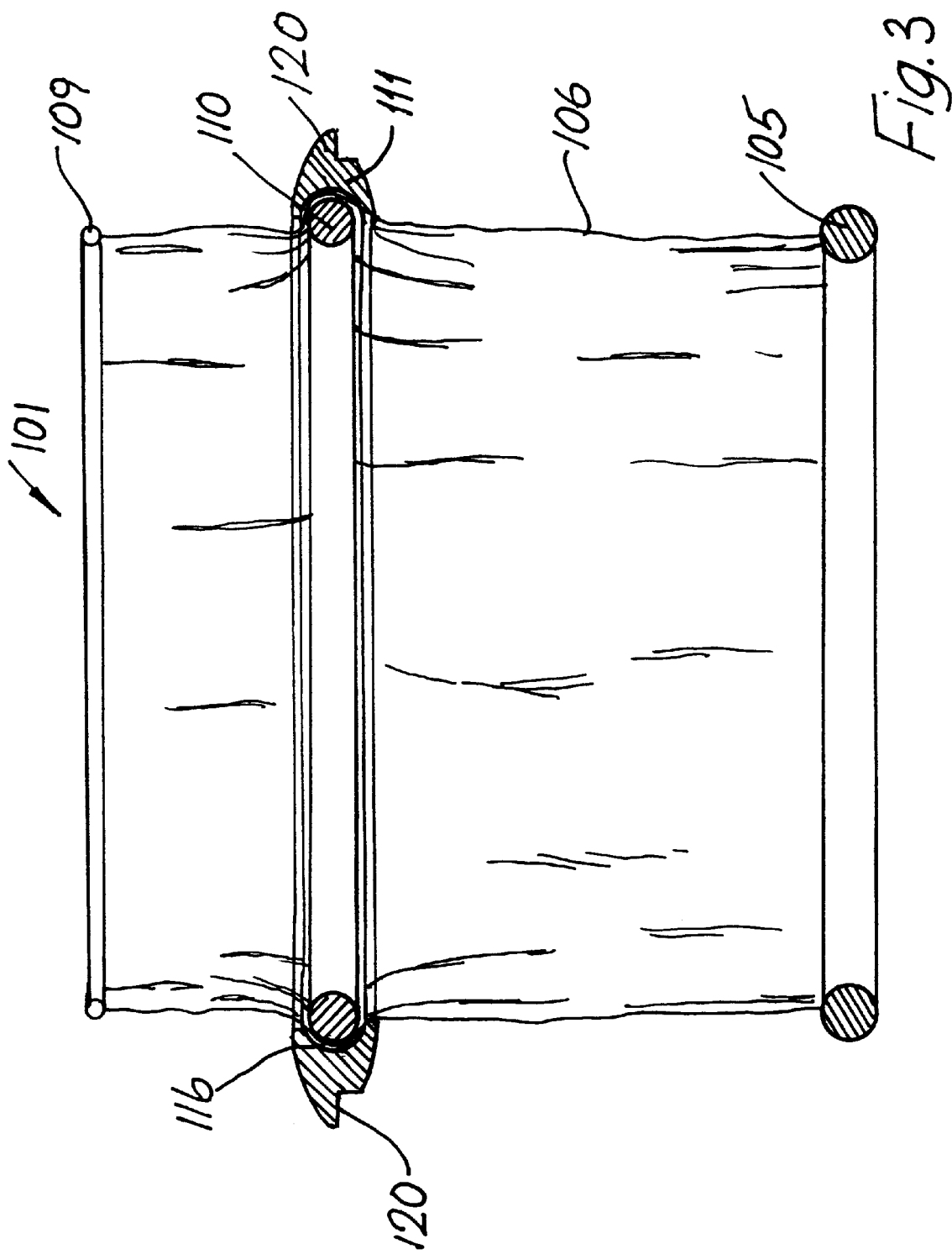
FIG. 3 is a side cross sectional view of the assembled retractor of FIG. 2.
Figure 4:
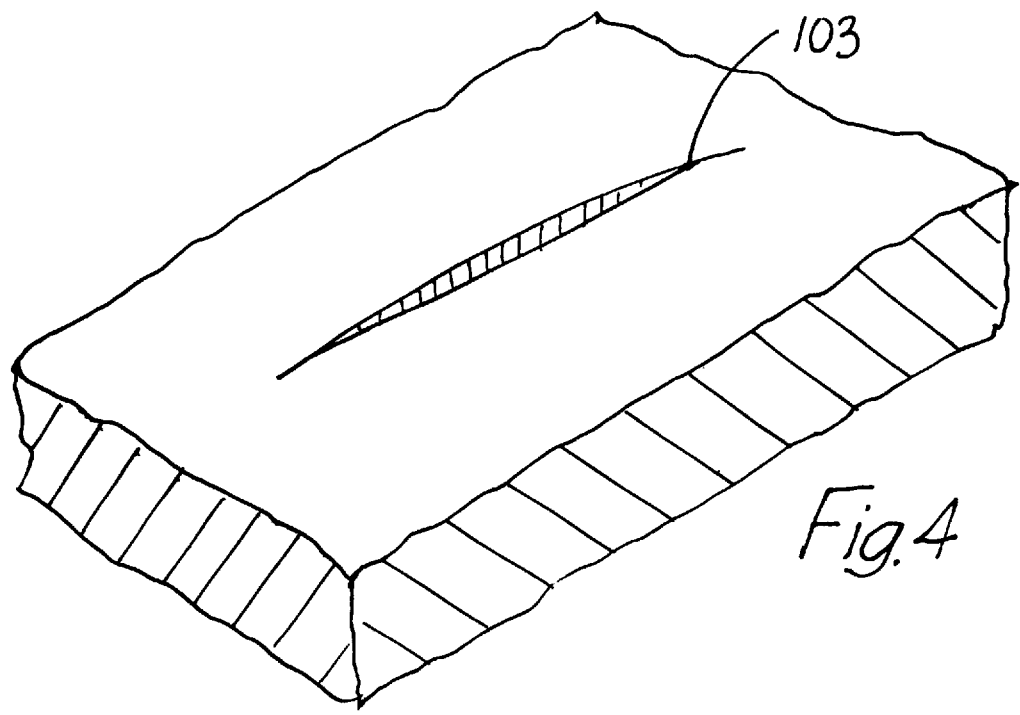
FIG. 4 is a perspective view of an unretracted wound opening.

Referring to FIGS. 1 to 13 there is illustrated a wound retractor 101 according to the invention, which in the case illustrated is used to retract the margins of a wound such as an abdominal wound opening 103, as illustrated in FIG. 4.

The retractor 101 comprises a distal anchoring member, in this case in the form of a resilient inner O-ring 105, for insertion into the wound opening 103, and a connecting means, in this case in the form of an elastomeric sleeve 106 which is substantially cylindrical. The sleeve 106 has an inner wound engaging portion and an outer portion, and the wound engaging portion is attached to the inner O-ring 105. The sleeve has an insertion configuration in which the inner wound engaging portion has a reduced radial dimension and a retracting configuration to retract the wound opening 103 laterally.

An external guide means is provided for the outer portion of the sleeve 106, and in this case the guide means comprises an inner ring part 110 and an outer ring part 111 between which the sleeve 106 is led. The retractor 101 includes external anchoring means for anchoring the sleeve 106 to maintain retraction of the wound opening 103, and in this case the anchoring means is provided by a plurality of anchor formations 120 on the outer surface of the outer ring part 111 (FIG. 2), the formations 120 extending radially outwardly to define hooks.

The outer ring part 111 is of the same annular shape as the inner ring part 110 but has a larger diameter and a recess 116. The inner ring part 110 is of a relatively stiff material and mates with the outer ring part 111 in the recess 116 to slidably retain the sleeve 106 therebetween, as illustrated in FIG. 3. In this case the ring parts 110, 111 are a relatively loose fit to facilitate movement of the ring parts 110, 111 relative to the sleeve 106 to shorten the axial extent of the sleeve 106 and thereby bias the wound engaging portion into the retracting configuration to retract the wound opening 103 laterally.

The ring parts 110, 111 are of a material with a low coefficient of friction such as Polytetrafluoroethylene (PTFE), PTFE is a tough, non-resilient material of moderate tensile strength and with excellent lubricity.

Figure 1:
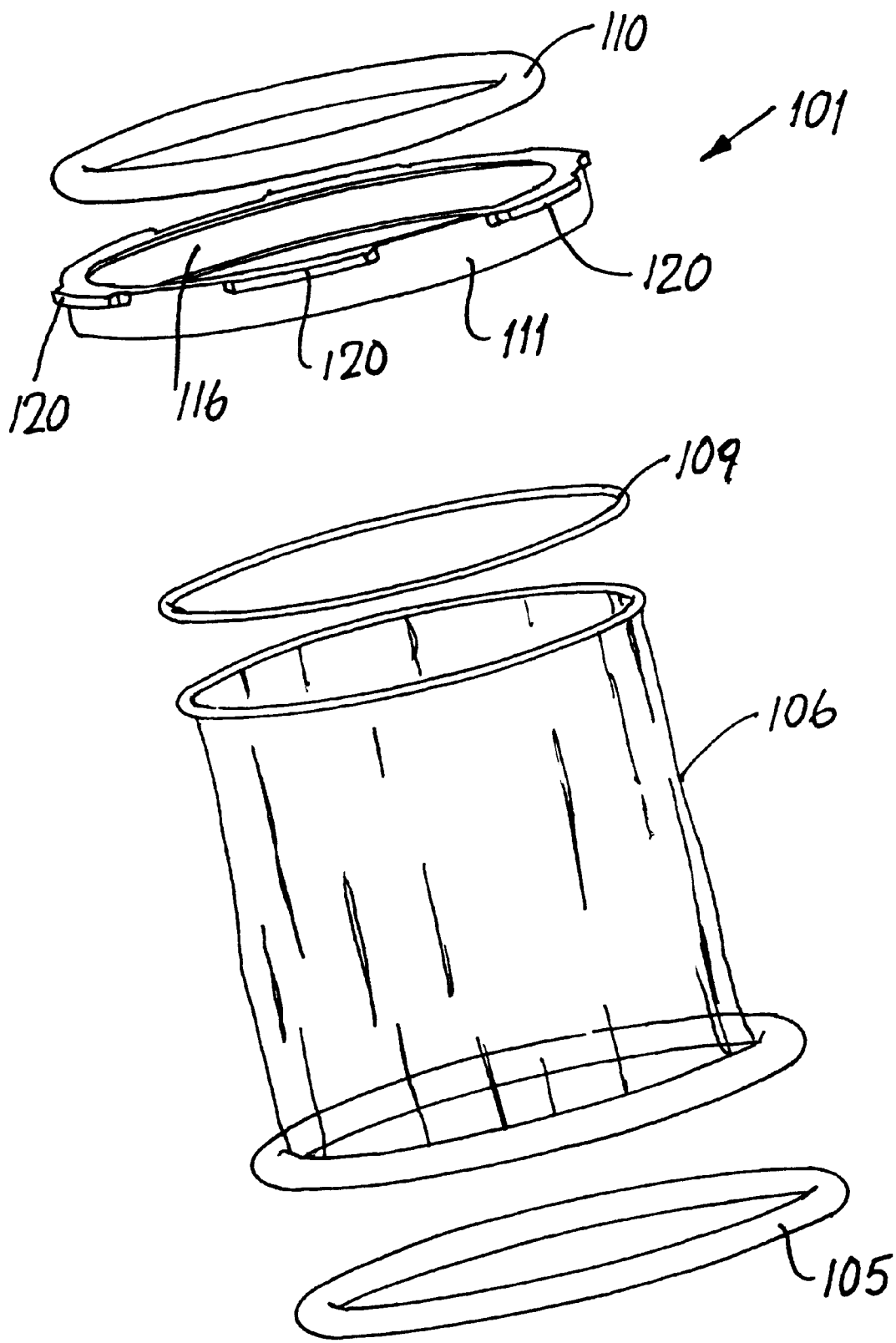
FIG. 1 is an exploded view of a wound retractor according to the invention.
Figure 2:
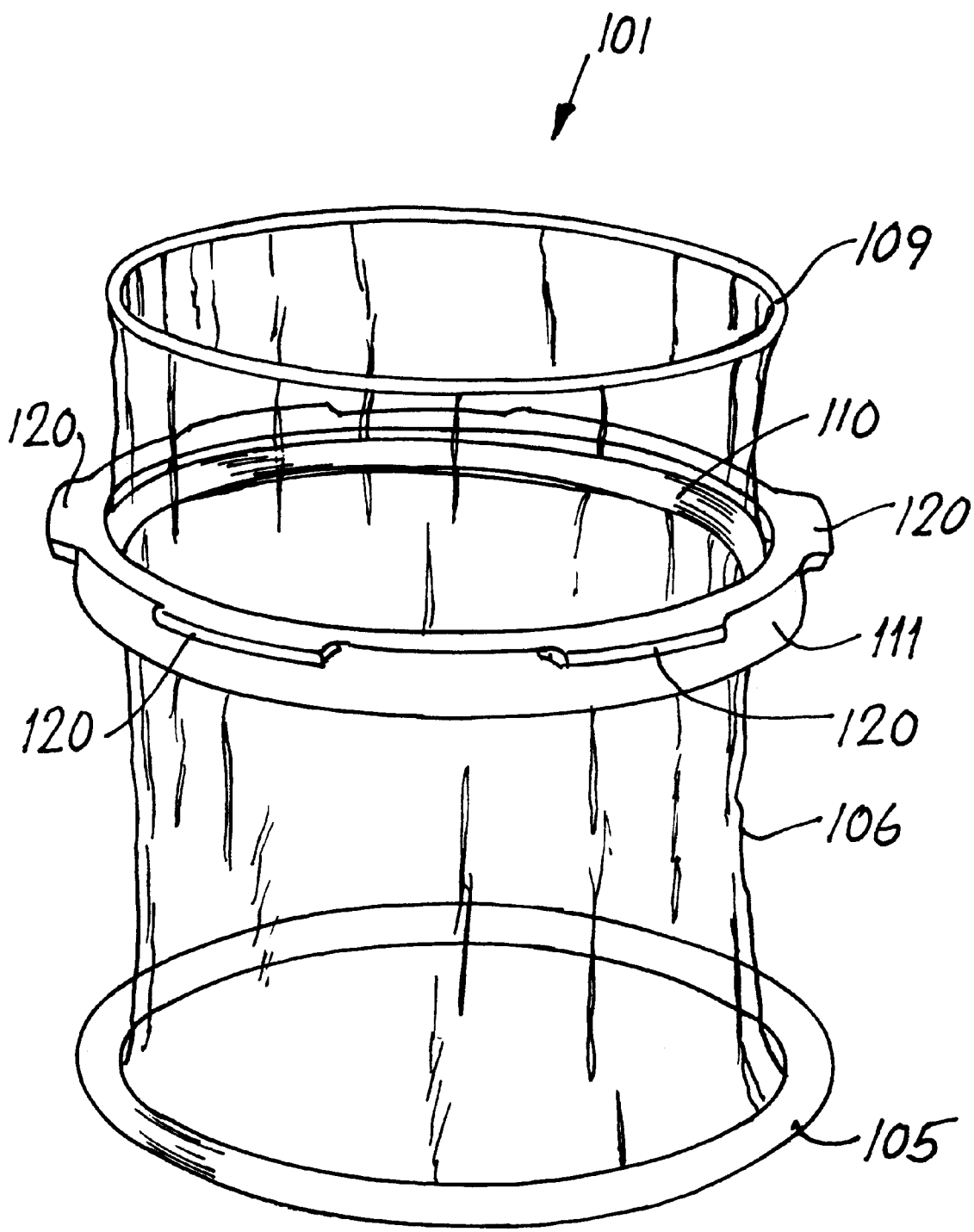
FIG. 2 is a perspective view of the retractor of FIG. 1 assembled.

The retractor 101 also includes a proximal reinforcing means for engagement with the anchor formations 120, and in this case the reinforcing means is provided by a resilient outer O-ring 109 of a material which is flexible relative to the inner O-ring 105. The outer O-ring 109 is attached to the proximal end of the sleeve 106, the rings 105, 109 helping to maintain the open shape of the sleeve 106 at its extremities (FIG. 2).

Figure 5:
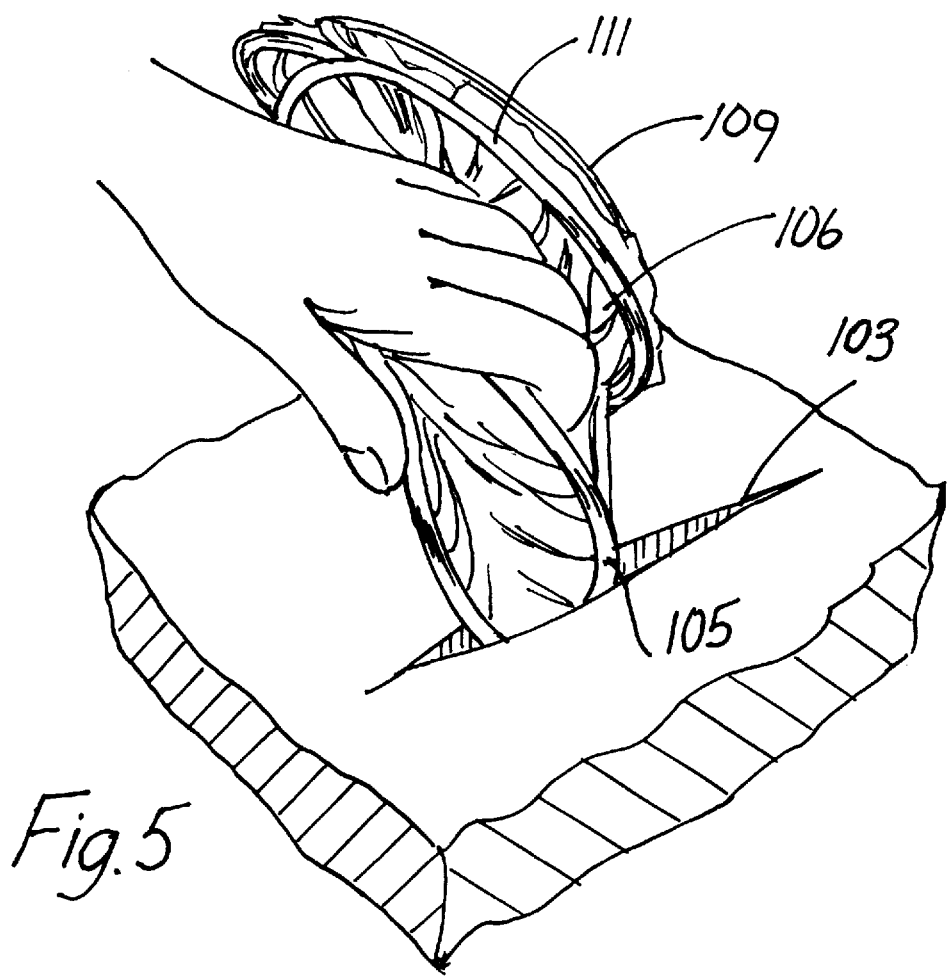
FIG. 5 is a perspective view illustrating insertion of part of the retractor of FIG. 2 into the wound opening.
Figure 6:
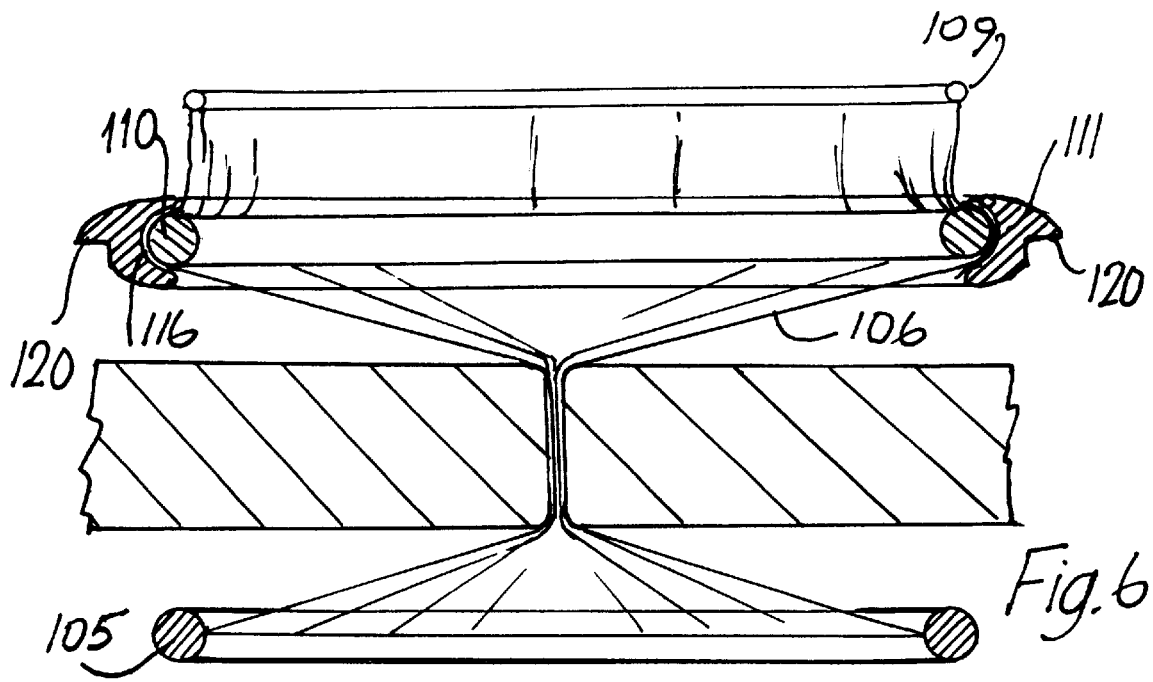
FIG. 6 is a side cross sectional view of the retractor of FIG. 2 after insertion.
Figure 7:
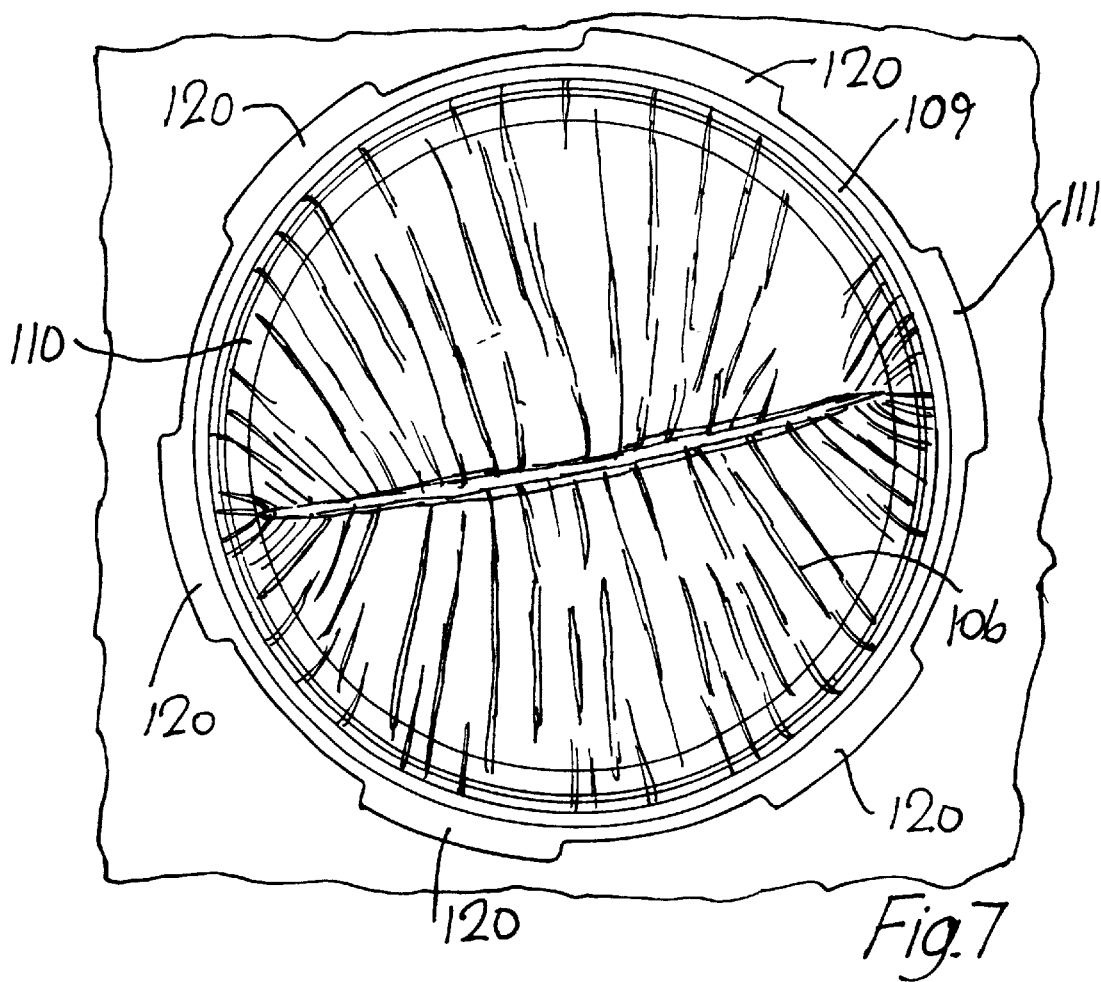
FIG. 7 is a plan view of the retractor of FIG. 2 after insertion.

In use the inner O-ring 105 and the sleeve 106 are squeezed into the insertion configuration for insertion of the inner O-ring 105 into the wound opening 103 (FIG. 5). The inner O-ring 105 is of a polymeric material which facilitates scrunching up of the inner O-ring 105 into a low-profile, elongate shape, as illustrated in FIG. 5, to facilitate ease of use. On release of the inner O-ring 105, the resilient O-ring 105 returns to its normal O-shape overlapping an inner edge of the wound opening 103 to safely anchor the retractor 101 in the wound, as illustrated in FIG. 6. As may be seen from FIGS. 6 and 7, after insertion of the inner O-ring 105, the wound opening 103 is substantially closed and the sleeve 106 is in a wrinkled compressed configuration.

Figure 8B:
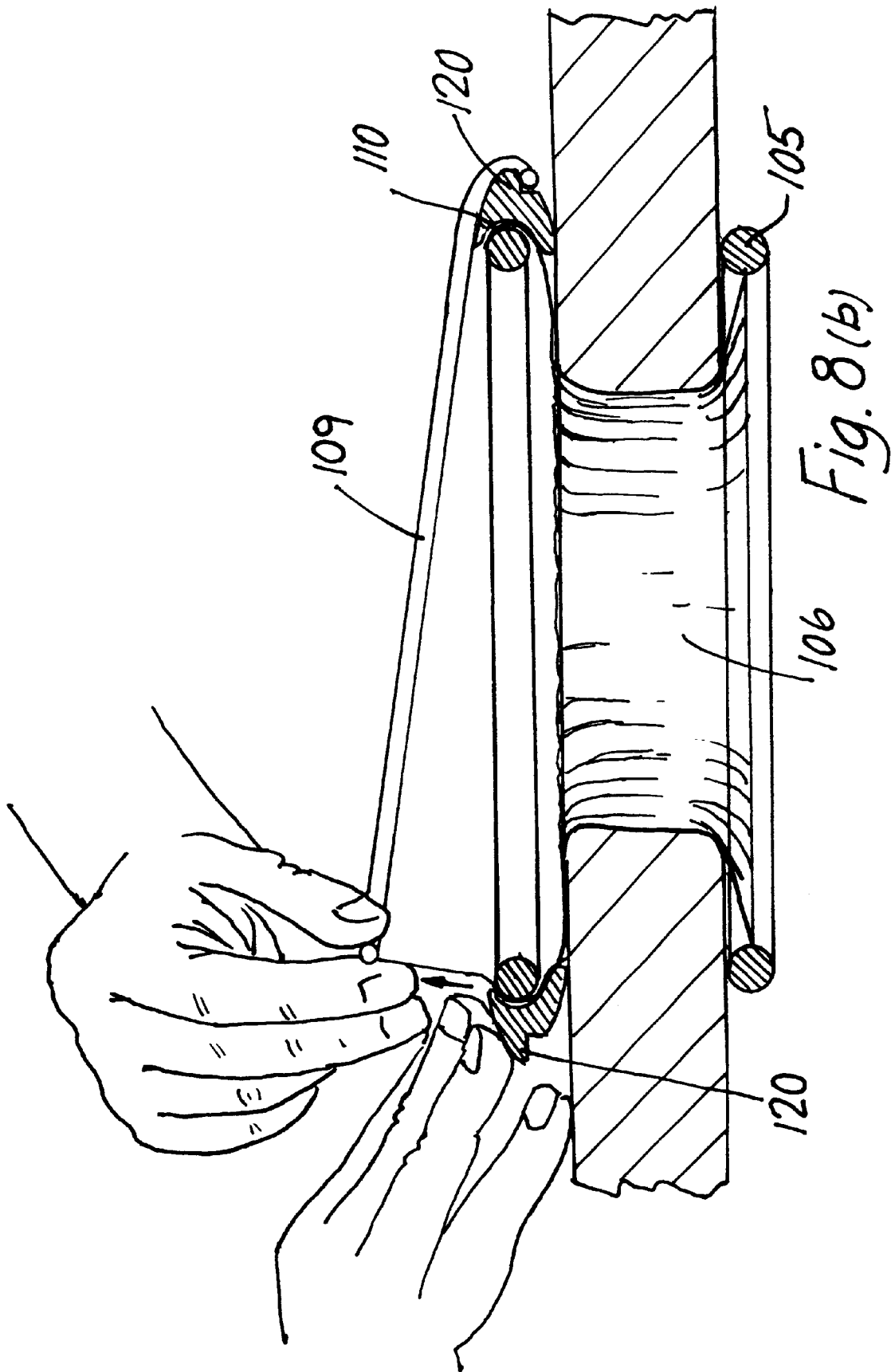

The sleeve 106 is then pulled while pushing the ring parts 110, 111 against the tissue surrounding the wound opening 103, as illustrated in FIG. 8(*a*), to shorten the axial extent of the sleeve 106 and thereby bias the wound engaging portion into the retracting configuration to retract laterally the right-band side (as viewed in FIG. 8(*a*)) of the wound opening 103, The right-hand side of the outer O-ring 109 is hooked around the formations 120 to maintain the right-hand side of the wound opening 103 retracted (FIG. 8(*b*)). The left-hand side of the sleeve 106 is then pulled while pushing the ring parts 110, 111 to retract laterally the left-hand side of the wound opening 103, as illustrated in FIG. 8(*b*). The left-hand side of the outer O-ring 109 is then hooked around the formations 120 to maintain the entire wound opening 103 fully retracted, as illustrated in FIGS. 9 and 10

The separate formations 120 and the configuration of the wound retractor 101 generally allow the sleeve 106 to be readily manipulated locally as illustrated in FIGS. 8(*a*) and 8(*b*) to provide an optimised retraction force. Thus, the manipulation is not simply limited to a single vertical axis but can be carried out in several different directions by pulling of the sleeve 106, and localised hooking of the outer O-ring 109 to the appropriate formation 120. In this way the retractor can be tailored to a particular application.

Figure 13:
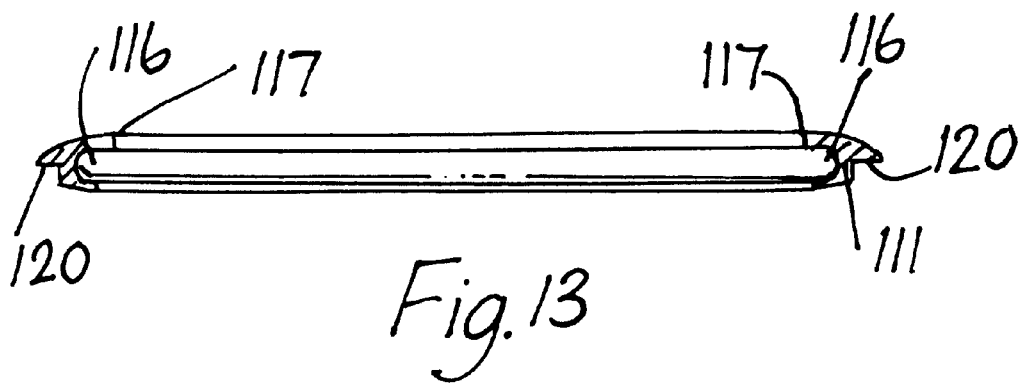
FIG. 13 is a cross sectional view along the line A—A in FIG. 11.

The recess 116 against which the sleeve 106 is slidably retained by the inner ring part 110 is C-shaped with an extended upper lip 117, as may be seen in FIG. 13. The upper lip 117 maintains the inner ring part 110 safely within the recess 116 regardless of the pulling direction or tensile pulling force exerted on the sleeve 106. It is preferable to pull the sleeve 106 in a non-vertical direction and to perform localised hooking of the outer O-ring 109, and the extended upper lip 117 encourages non-vertical pulling of the sleeve 106.

Figure 9:
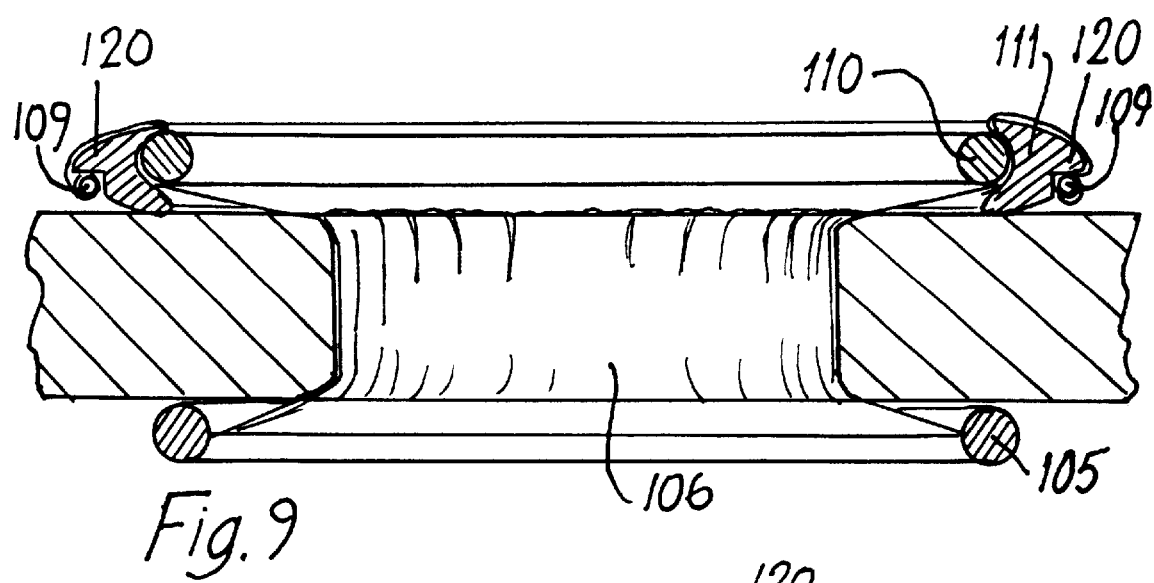
FIG. 9 is a side cross sectional view of the retractor of FIG. 2 after lateral retraction of the wound opening.
Figure 10:
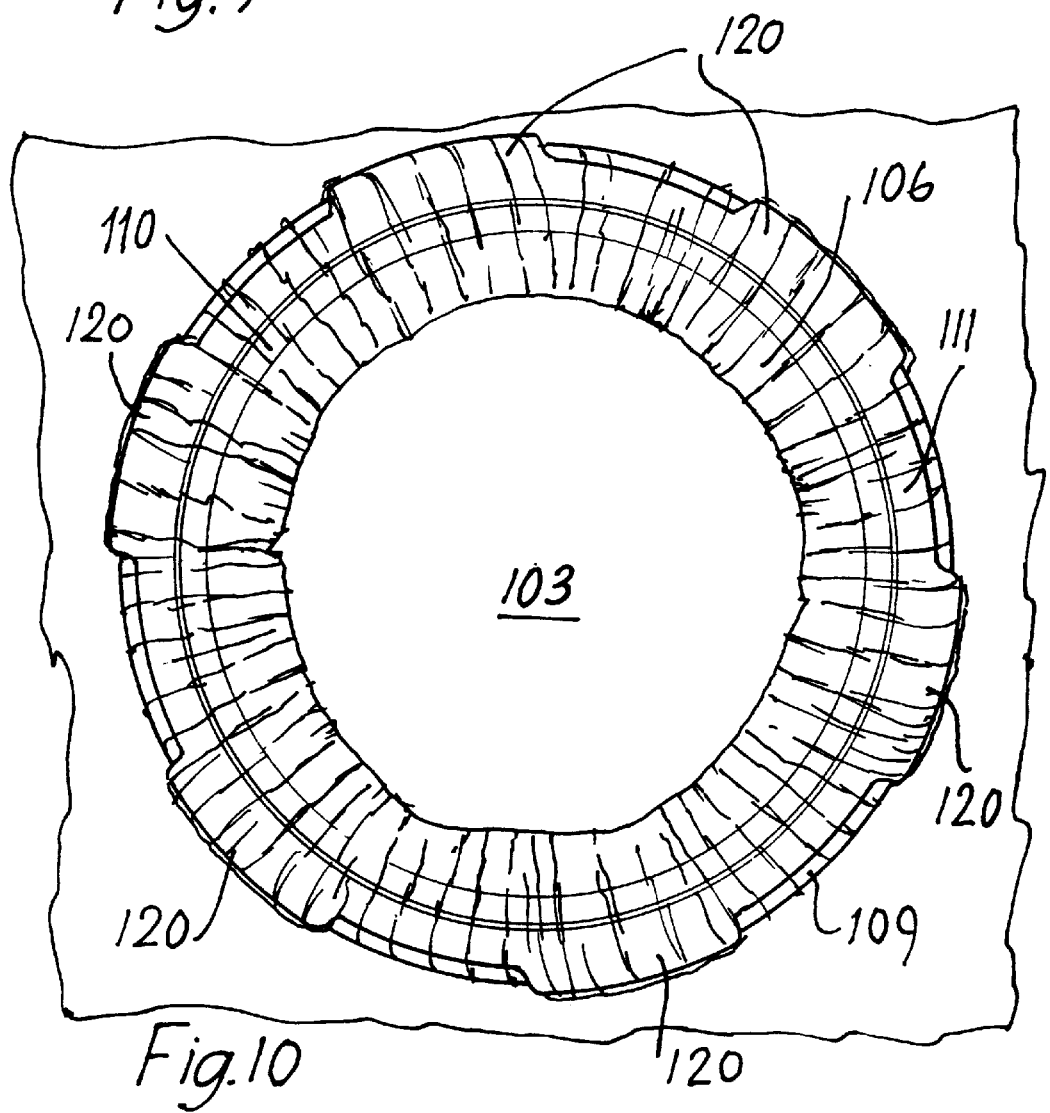
FIG. 10 is a plan view of the retractor of FIG. 2 after lateral retraction of the wound opening.
Figure 11:
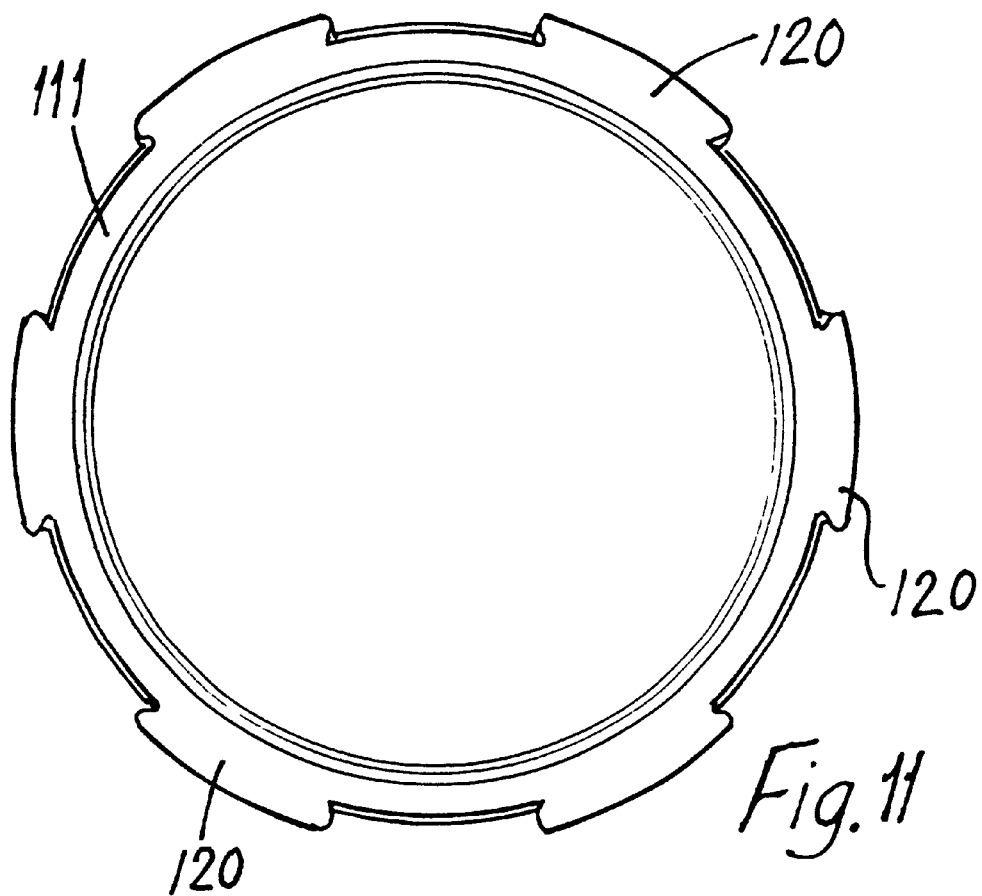
FIG. 11 is a plan view of a part of a guide means of the retractor of FIG. 2.
Figure 12:
FIG. 12 is a side view of the part of FIG. 11.

The elastomeric sleeve 106 lines the side of the retracted wound opening 103, as illustrated in FIG. 9, and thus acts both as a means of wound retraction and wound protection.

The surgical wound retractor is of simple construction, is easy to use and can be manufactured inexpensively to provide a disposable unit.

A single wound retractor according to the invention may be used for a wide range of incision sizes and to achieve a range of different localised retraction forces which are required to accommodate the incision, the patient anatomy and the surgical procedure to be performed.

Figure 14:
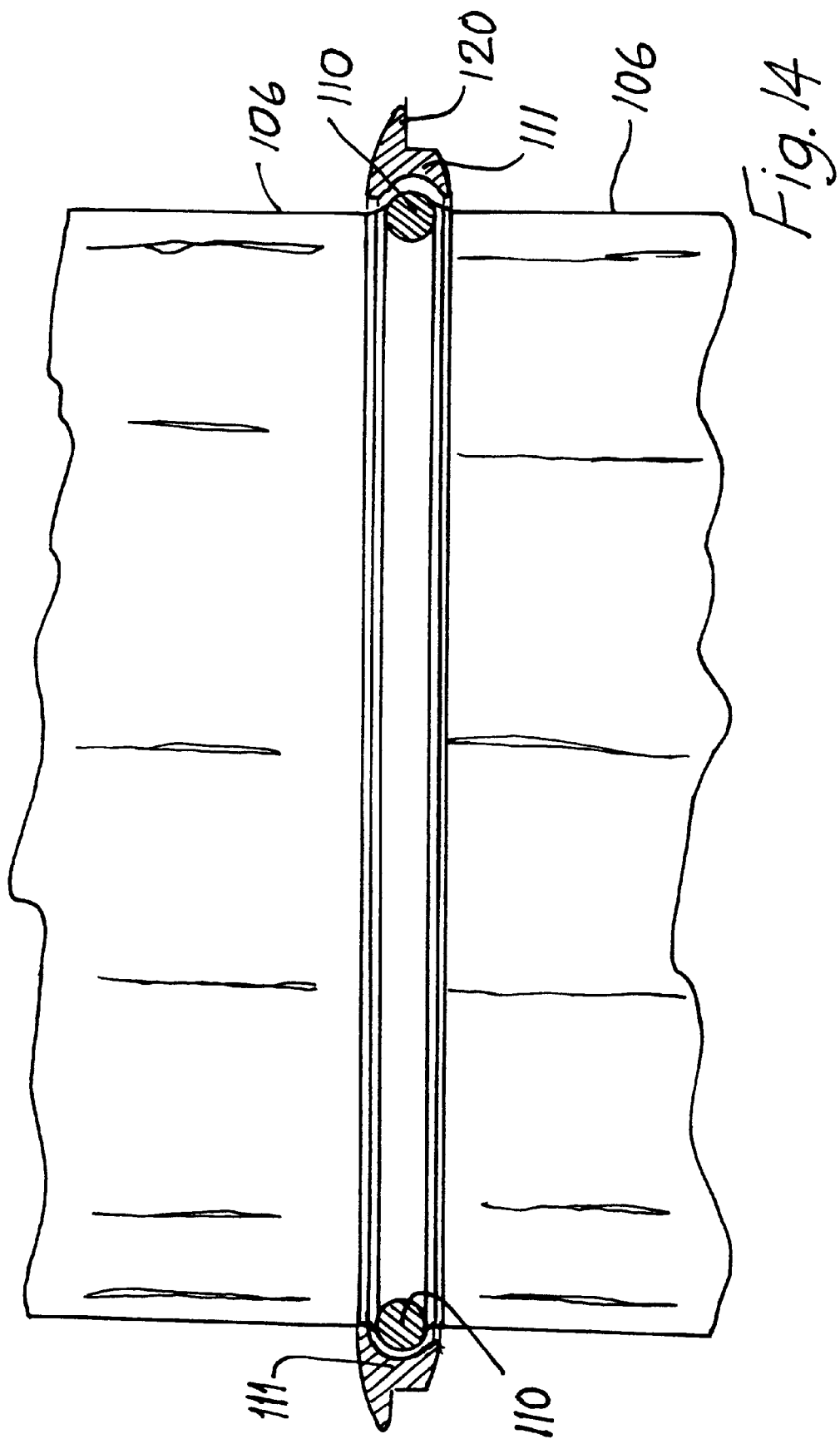
FIG. 14 is a cross sectional view of part of another wound retractor according to the invention.
Figure 15:
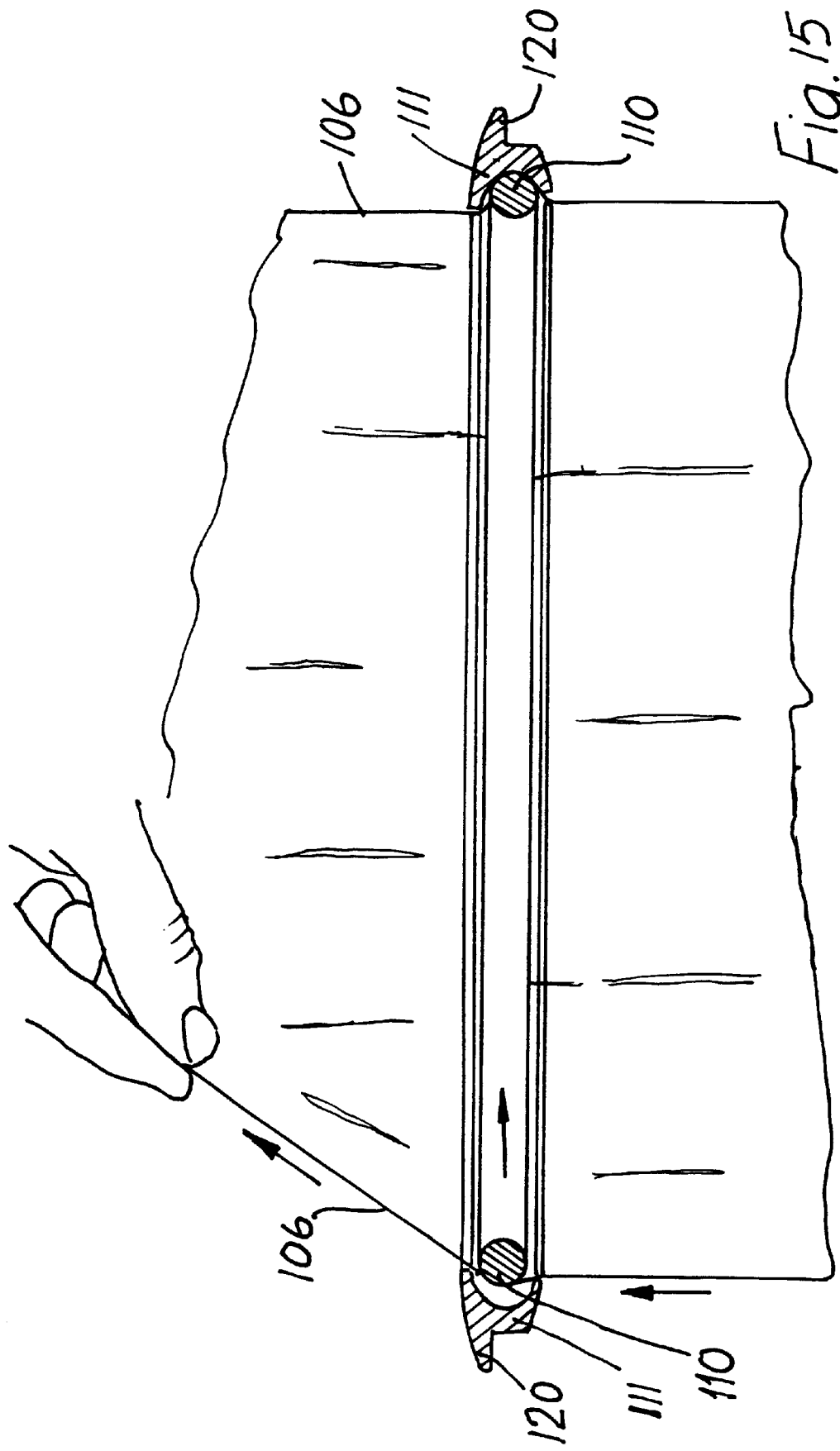
FIG. 15 is a cross sectional view of the retractor of FIG. 14, in use.
Figure 16:
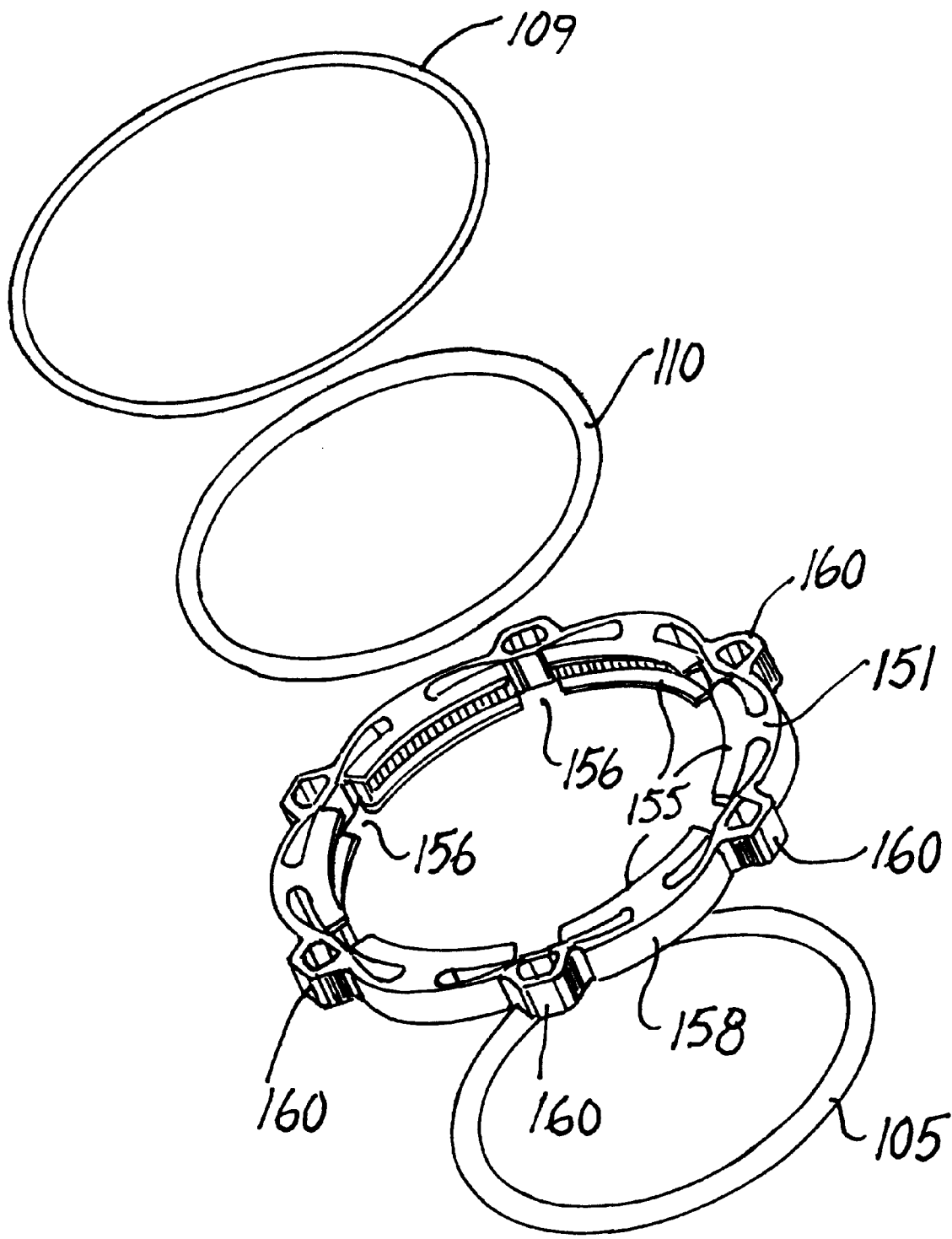
FIG. 16 is an exploded view of parts of another wound retractor according to the invention.
Figure 17:
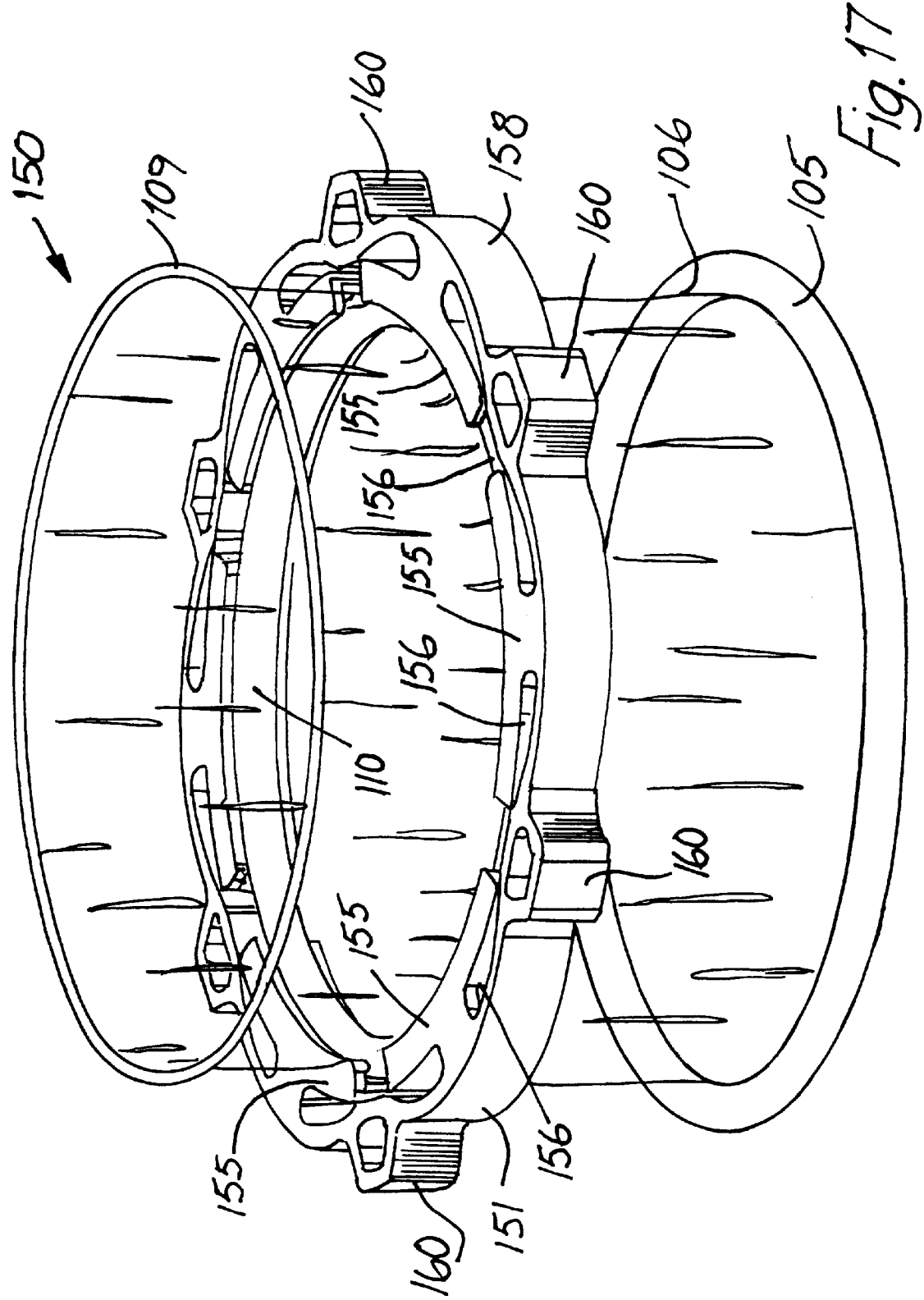
FIG. 17 is a perspective view of the wound retractor of FIG. 16 assembled.
Figure 18:
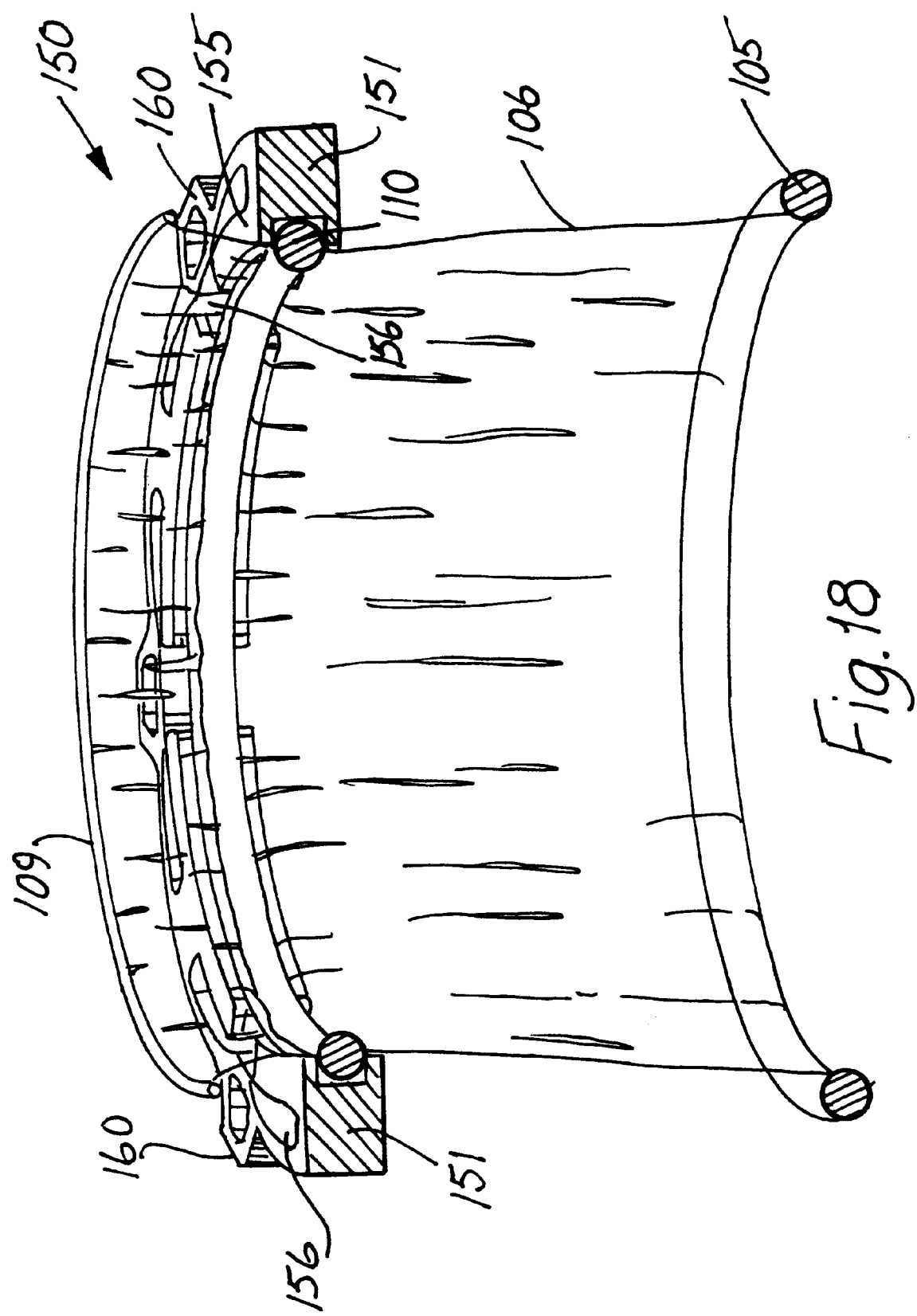
FIGS. 18 and 19 are perspective cut-away views of the retractor of FIG. 17 in different positions.
Figure 19:
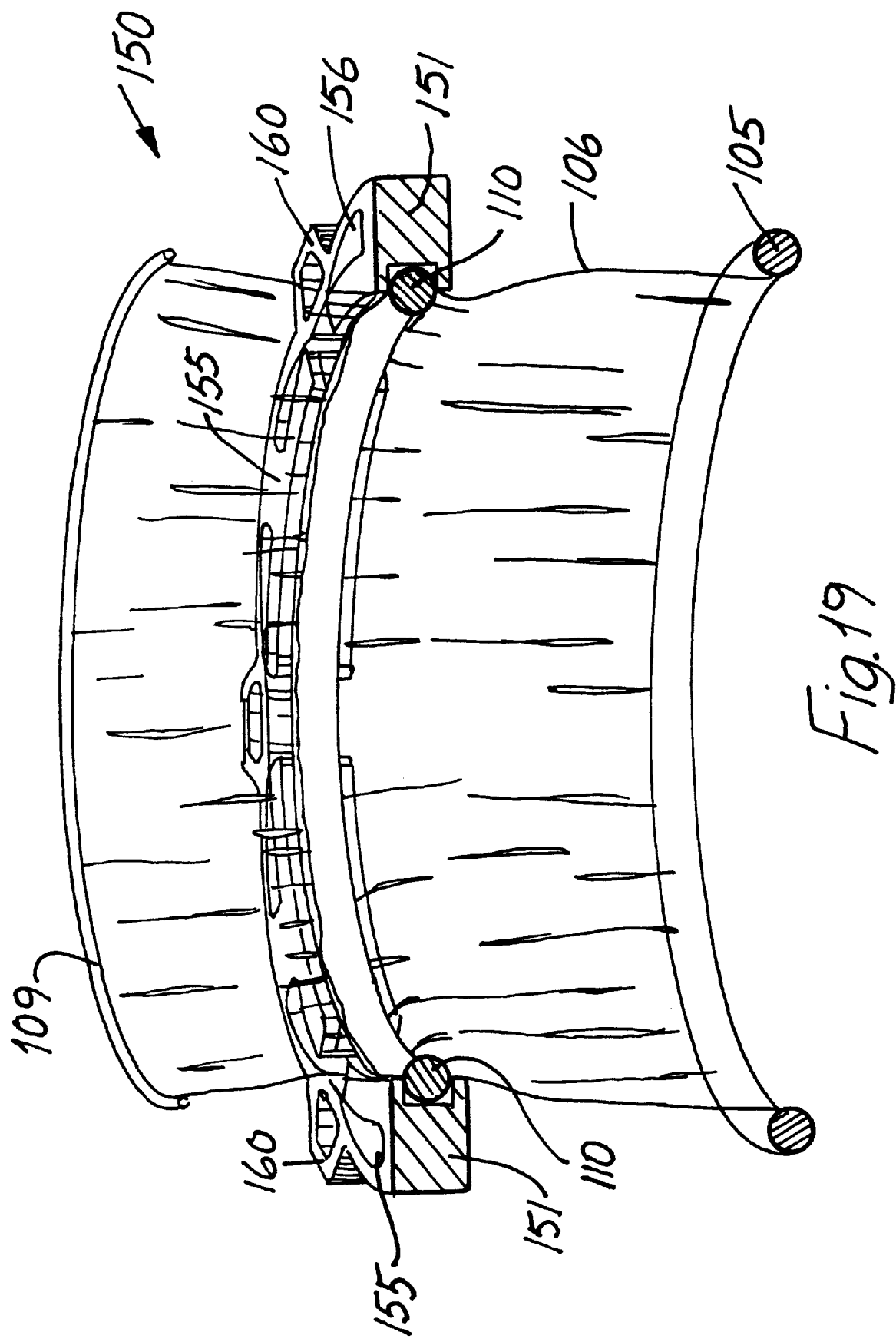

In the retractor of FIGS. 1 to 10 the sleeve 106 is a relatively tight fit between the outer and inner guide ring parts 110,111. It is also possible to configure the outer and inner ring parts 110, 111 so that the inner ring part 110 is a relatively looser fit in the outer part 111. In this case the guide means comprises an outer ring part or other annular shape within which slides a second component. The second component is of the same annular shape as the outer ring part but with a lesser diameter and has an exterior compartmental recess designed so that the outer ring part fits loosely around the second component and both can easily slide relative to each other. The components fit loosely together so that an elastomeric sleeve can fit in the gap between them and slide therein. Such an arrangement is illustrated in FIGS. 14 and 15. On puffing of a local area of the sleeve 106 as indicated in FIG. 15 the inner ring part 110 moves to an appropriate side clamping the sleeve 106 at that opposite side while allowing local manipulation of the gripped section of sleeve allowing the local retraction force at the gripped side to be optimised prior to anchoring of the sleeve at that side. This procedure may be repeated at other local regions of the sleeve 106.

Referring to FIGS. 16 to 23 there is illustrated another wound retractor 150 according to the invention which is similar to the wound retractor 101 described with reference to FIGS. 1 to 13 and like parts are assigned the same reference numerals in FIGS. 16 to 23.

In this case the guide means comprises the inner ring part 110 and an outer PTFE ring part 151 configured so that the outer ring part 151 engages the inner ring part 110 at a plurality of discrete points circumferentially spaced around the outer ring part 151 to clamp the sleeve 106 between the inner and outer ring parts 110, 151 at each discrete point. The outer ring part 151 comprises a plurality of interconnected segments 155 circumferentially spaced around the outer ring part 151 which press on the inner ring part 110 to clamp the sleeve 106 and are independently movable to facilitate localised release of the sleeve 106 for adjustment of the retraction force. Cut-out T-slots 156 are provided between the segments 155 and a main body 158 of the outer ring part 151, and handles 160 project radially outwardly of the main body 158 of the outer ring part 151 intermediate the segments 155.

In use, adjacent handles 160 are manually gripped as illustrated in FIG. 20 to apply a release force in the direction of arrows A which in turn pulls the local segment 155 in the direction of arrow B from a rest position clamping the sleeve 106 (FIGS. 20 and 21) to a release position (FIGS. 22 and 23) in which the sleeve 106 is readily pulled and manipulated locally. By releasing the clamp between the inner ring part 110 and the segment 155 the elastomeric sleeve 106 in readily slid from one position to another. This arrangement is particularly advantageous to facilitate local manipulation of the retraction force.

In general, the wound retractor 150 according to the invention is employed by inserting the inner O-ring 105 into a wound opening 103 and pulling the sleeve 106 so that the inner O-ring 105 lies flat against the interior anatomical surface. The inner O-ring 105 anchors the retractor 150 in the wound and prevents the elastomeric sleeve 106 from slipping out of the wound opening 103. The guide means clamp is then released by squeezing handles 160 and the ring parts 110, 151 are slid down the elastomeric sleeve 106 until they come into contact with the exterior anatomical surface. Retraction is achieved by pulling the sleeve 106 to shorten the distance between the inner O-ring 105 and the ring parts 110, 151 and thereby displace the elastomeric sleeve 106 laterally and with it the margins of the wound opening 103. The elastomeric sleeve 106 is anchored to maintain retraction of the wound opening 103 by releasing the handles 160 of the outer ring part 151 to clamp the sleeve 106.

Figure 24:
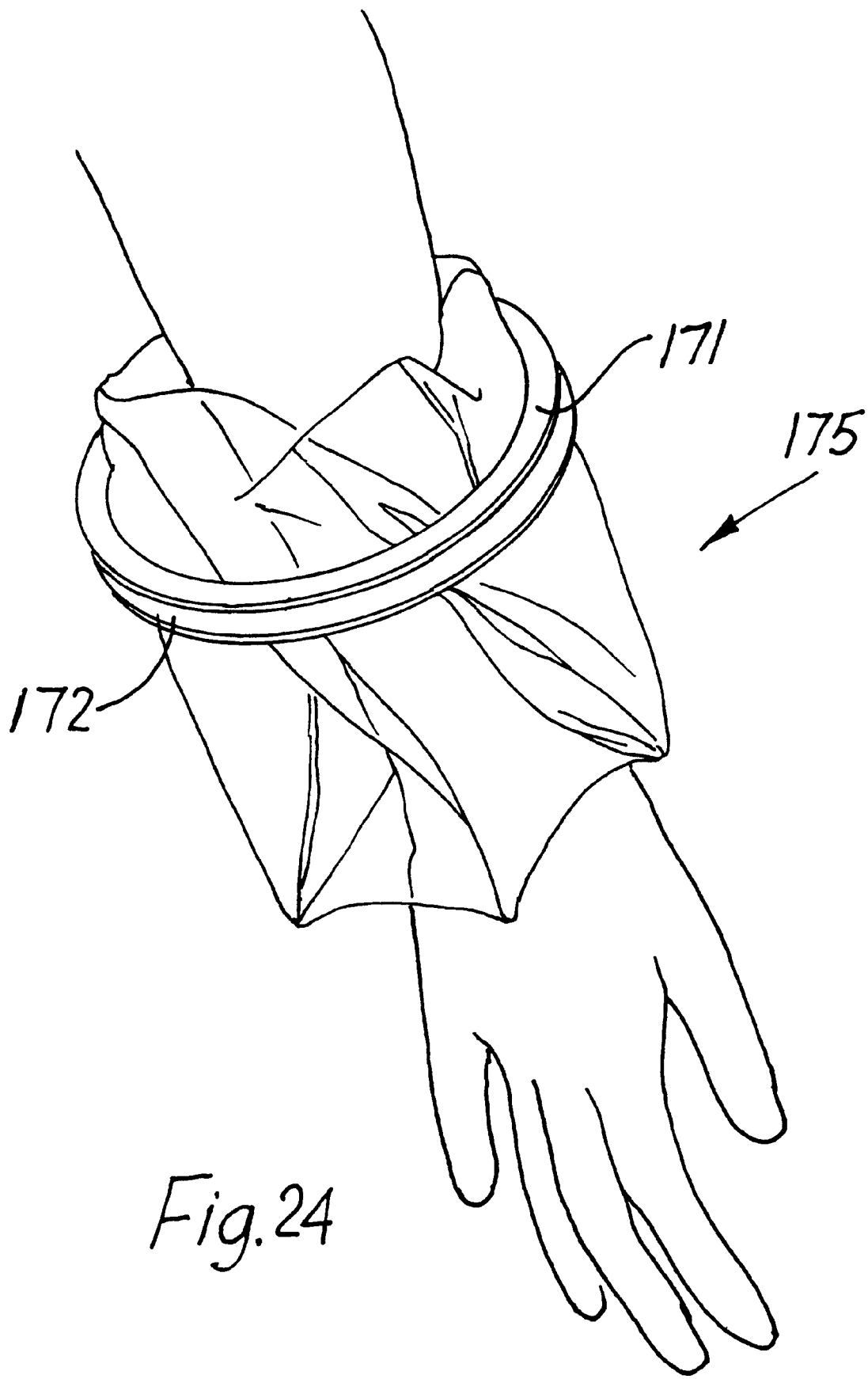
FIG. 24 is a perspective view of a hand access device for use with a wound retractor according to the invention.
Figure 25:
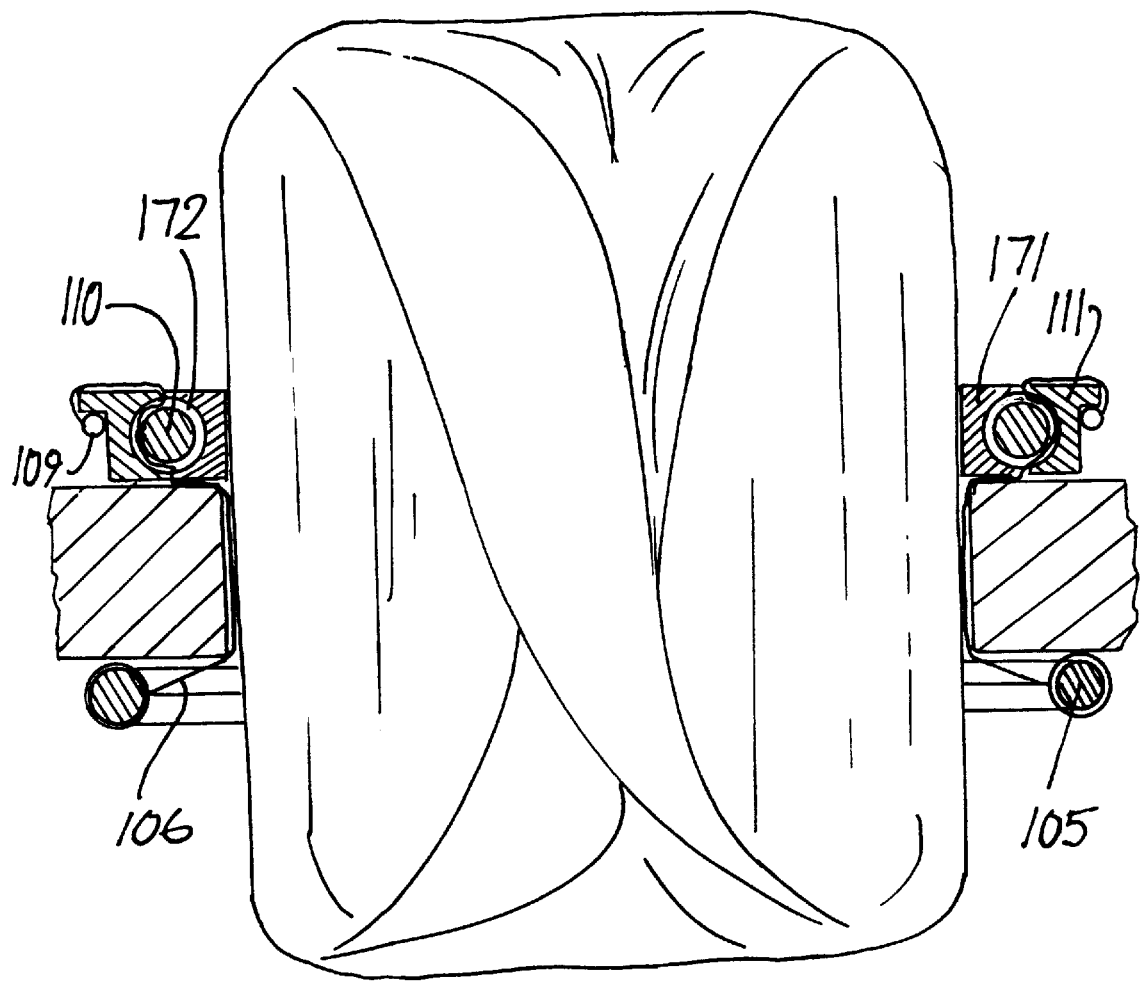
FIG. 25 is a side cross sectional view of the retractor of FIG. 2 with the hand access device of FIG. 24 in position.
Figure 26:
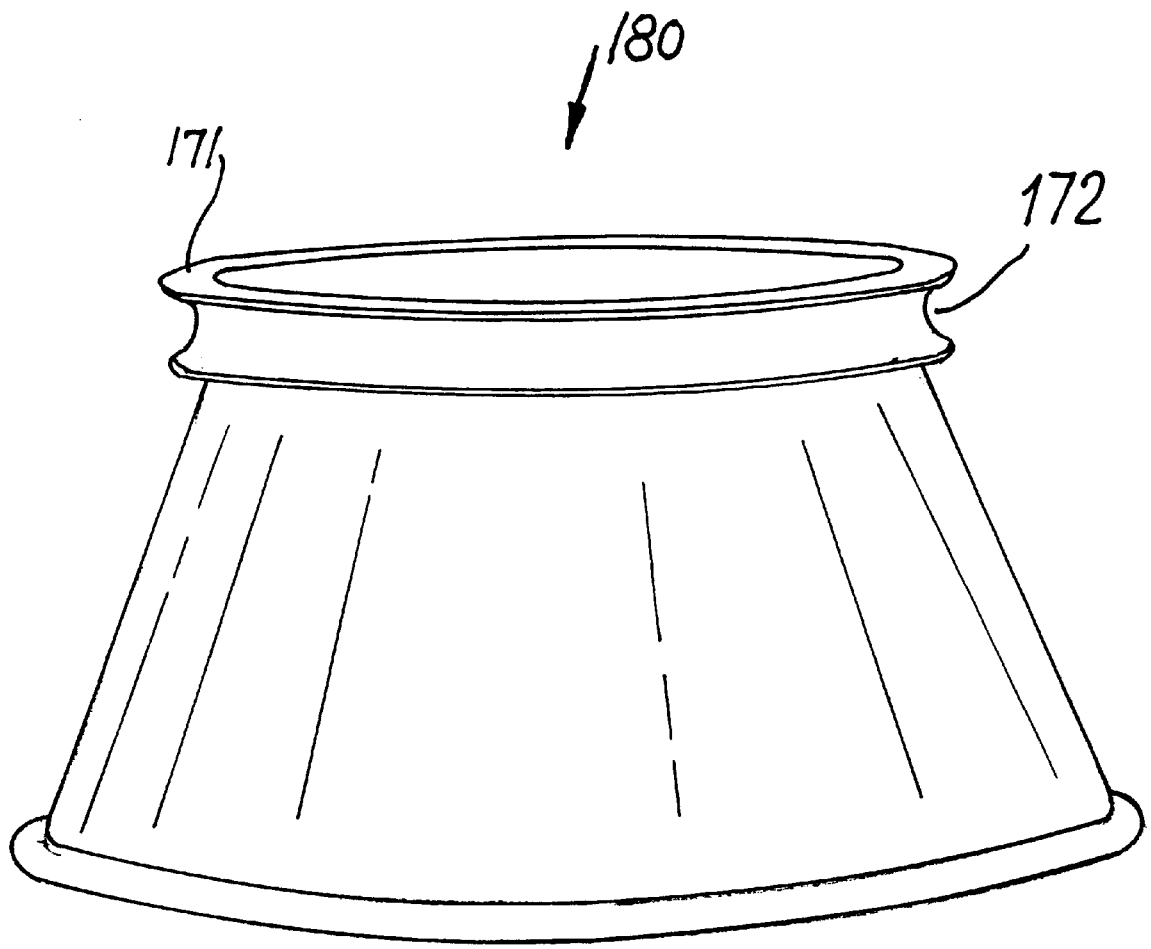
FIG. 26 is a perspective view of a drape for use with a wound retractor according to the invention.
Figure 27:
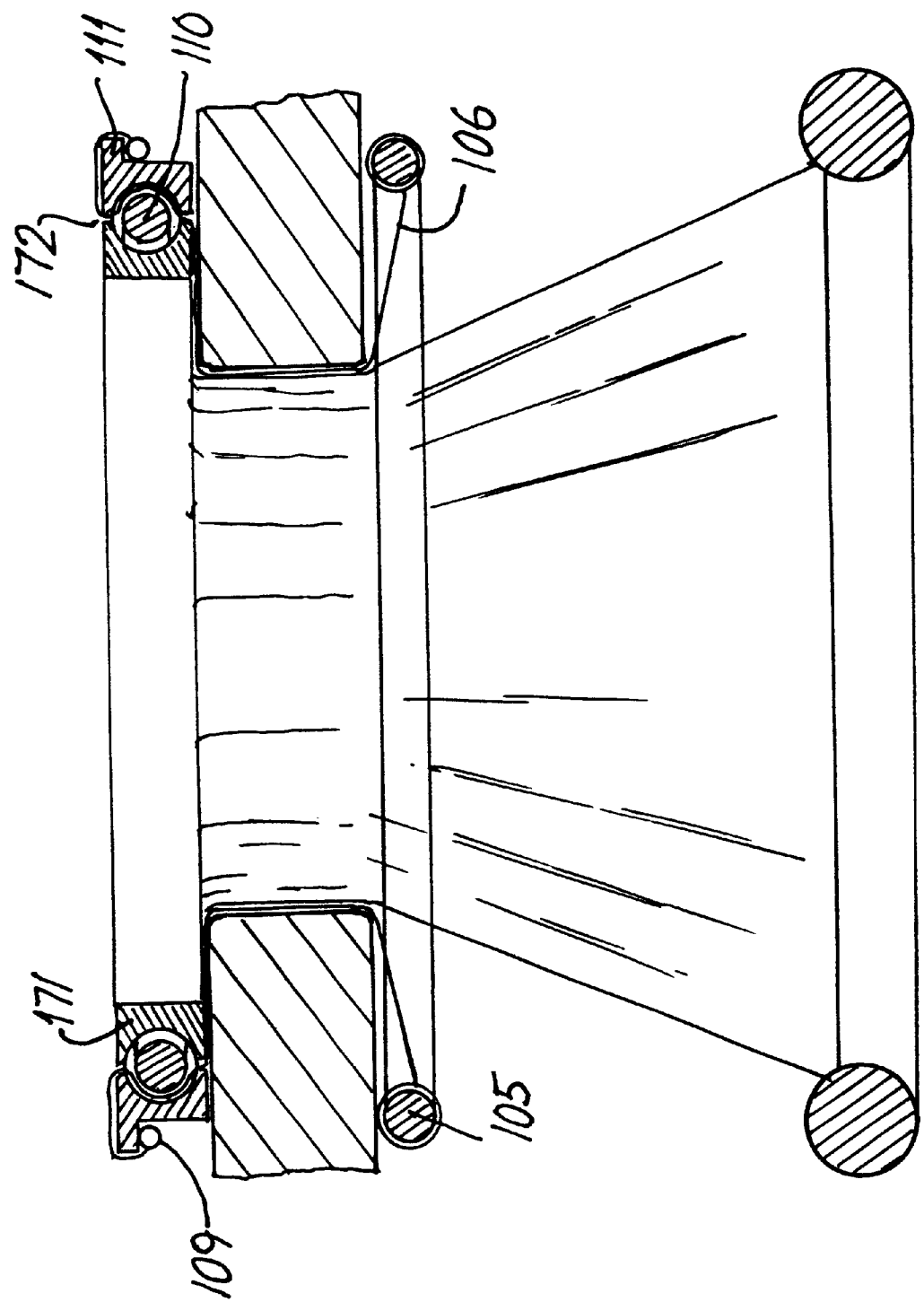
FIG. 27 is a side cross sectional view of the retractor of FIG. 2 with the drape of FIG. 26 in position.
Figure 28:
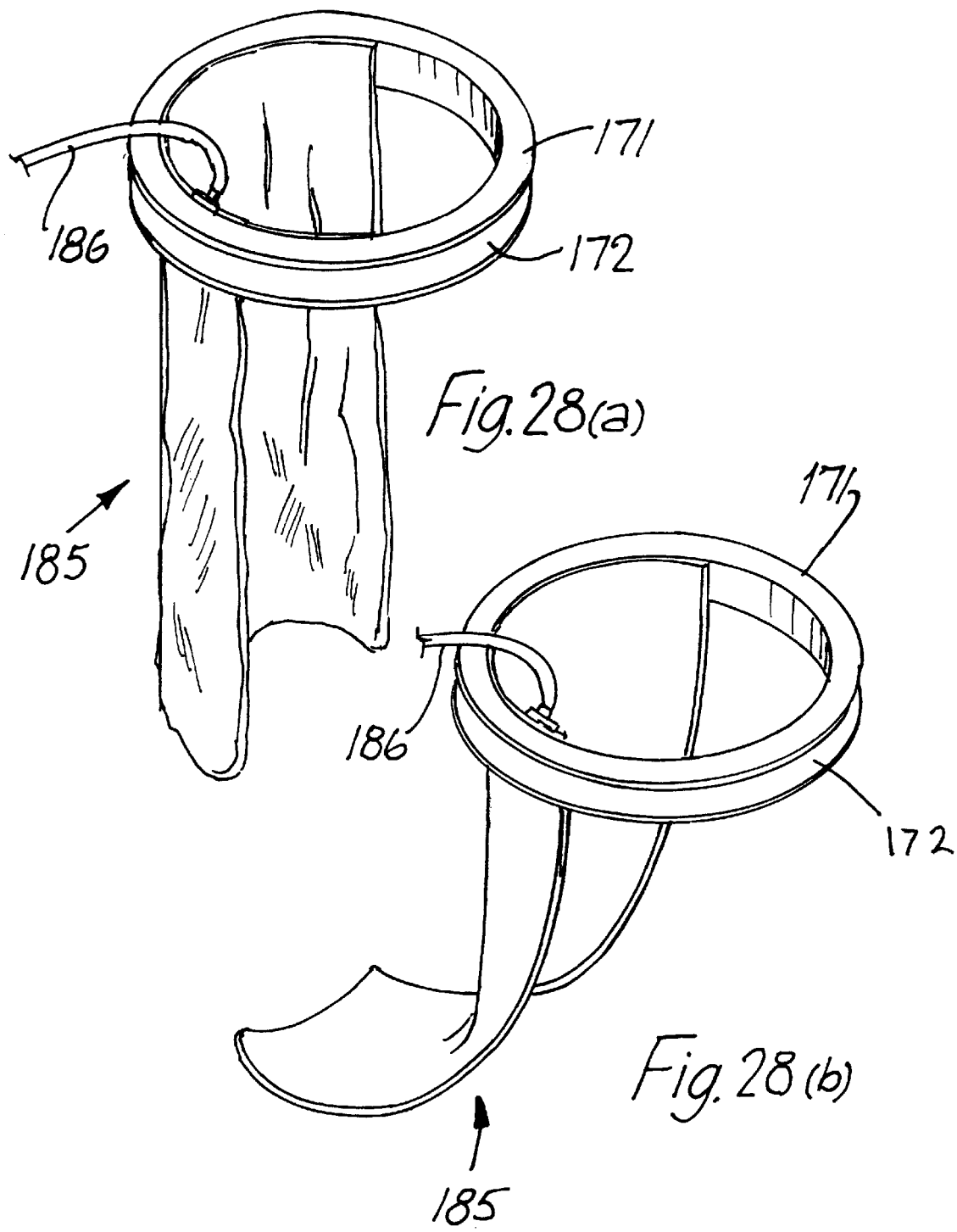
FIG. 28(a) is a perspective view of a form retaining device in a pliable state for use with a wound retractor according to the invention.
FIG. 28(b) is a perspective view of the form retaining device of FIG. 28(a) in a stiff state.
Figure 29:
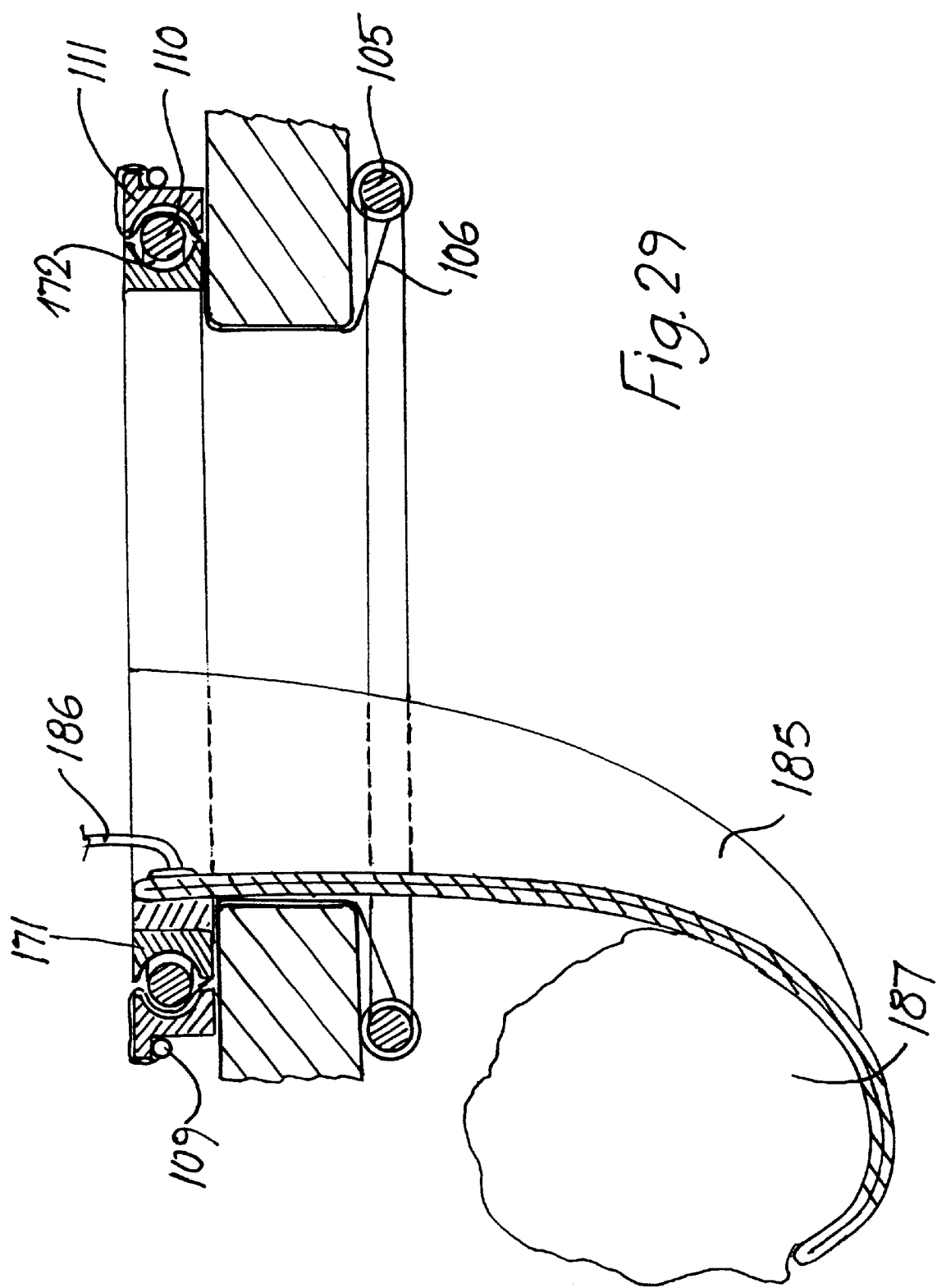
FIG. 29 is a side cross sectional view of the retractor of FIG. 2 with the stiffened form retaining device of FIG. 28(b) in position.

The wound retractors according to the invention also provides a platform on which a wide range of devices may be mounted. In one case the platform is provided by an inner projection part of the inner ring part 110 on which a ring part 171 with a complementary recess 172 may be easily fitted somewhat in the manner of a snap-type engagement. Various devices may be provided with such a ring part 171. For example, as illustrated in FIGS. 24 and 25 the device may be a hand access device 175 for use in laparoscopic surgery. Alternatively the device may be a drape 180 (FIGS. 26 and 27) or a form retaining device 185 which is manipulated to the form of, for example, an organ 187 to be held back and from which air is then evacuated along an evacuation line 186 to retain the desired organ holding configuration (FIGS. 28 and 29).

Figure 30:
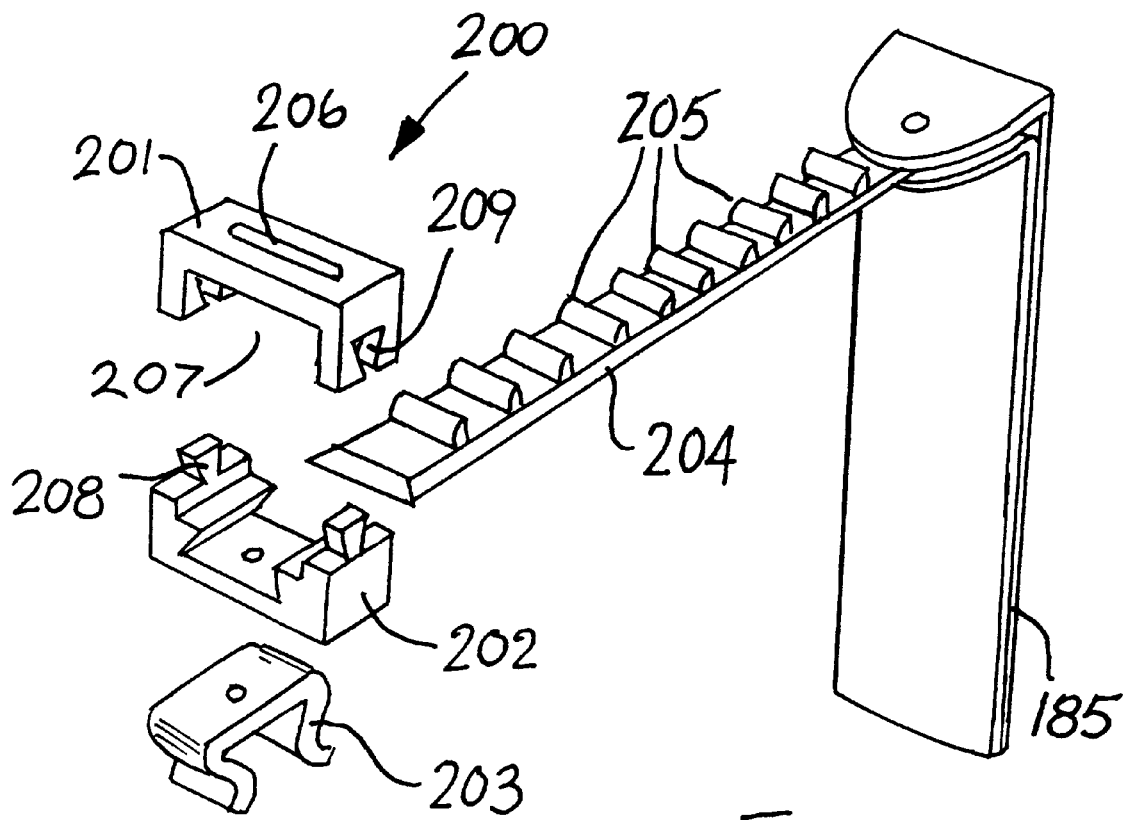
FIG. 30 is an exploded view of the form retaining device of FIG. 28 and a clamp.
Figure 31:
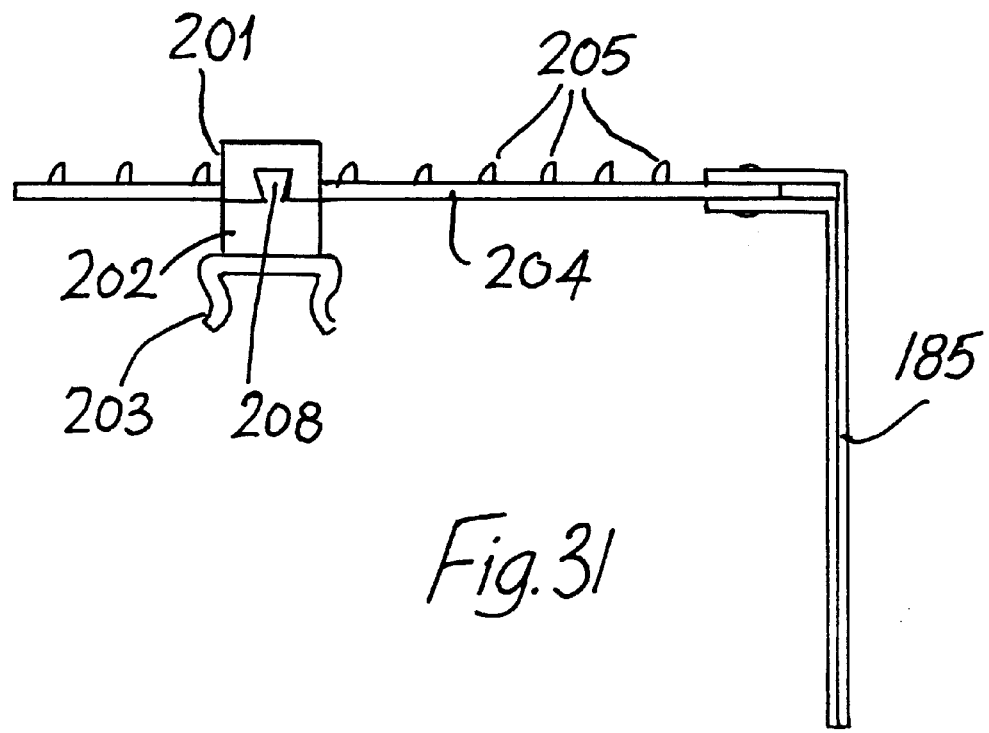
FIG. 31 is a side view of the form retaining device of FIG. 28 and the clamp of FIG. 31.
Figure 32:
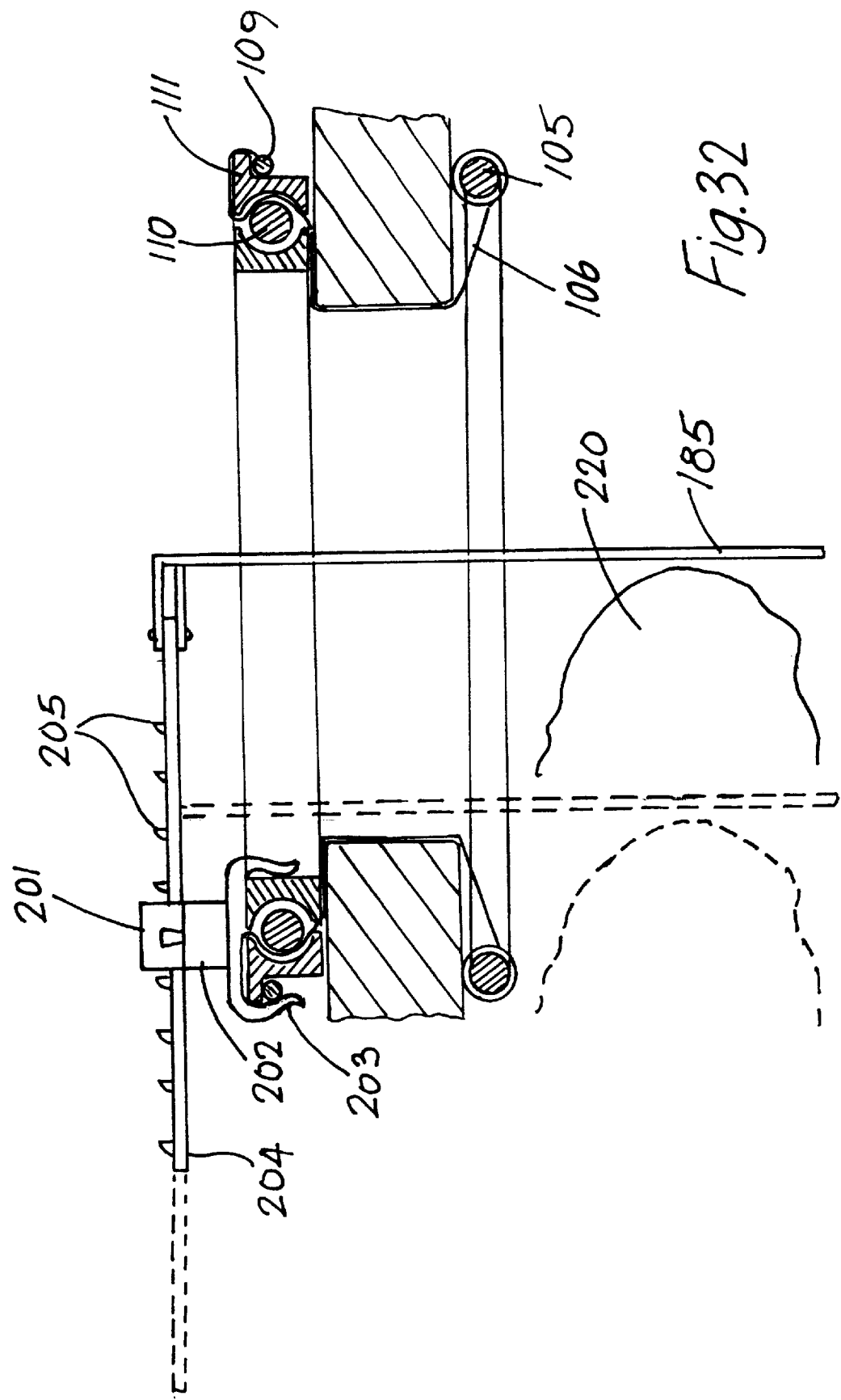
FIG. 32 is a side cross sectional view of the retractor of FIG. 2 with the form retaining device of FIG. 28 and the clamp of FIG. 30 in position.

The platform may alternatively be provided by a clamp 200 as illustrated in FIGS. 30 to 32. The clamp 200 comprises an upper jaw 201, a lower jaw 202, a clip 203 and an arm 204.

The clamp 200 is assembled by screwing the clip 203 to the base of the lower jaw 202, sliding the upper jaw 201 over the lower jaw 202 to engage the male projecting parts 208 within the corresponding female recesses 209 and extending the are 204 through the open mouth 207 between the upper and lower jaws 201, 202. A plurality of teeth 205 are provided on the arm 204, the teeth 205 being sized to project upwardly through a recess 206 in the upper jaw 201 when the arm 204 is within the open mouth 207. The teeth 205, as shown more clearly in FIG. 31, are shaped such that the arm 204 may be pulled back through the open mouth 207 in a ratchet-type arrangement but cannot be pushed forward again. A suitable material for the clamp components 201, 202, 203, 204 is spring steel.

Various devices may be attached to the free end of the arm 204, such as the form retaining device 185, as illustrated in FIG. 30. In use, the clip 203 is securely fixed to the wound retractor 101 by a snap-fit arrangement with the form retaining device 185 extending into the wound opening 103, as illustrated in FIG. 31. The form retaining device 185 is then ratcheted laterally across the wound opening 103 to retract for example, an internal organ 220, The ratchet configuration of the clamp 200 and the rigidity of the form retaining device 185 ensure that the internal organ 220 is securely maintained in a desired position.

It will be appreciated that any of the embodiments of the wound retractor according to the invention may be used as a platform on which-to mount other devices for use in various surgical procedures. Such devices may include: a capping device to cover the incision site or orifice; a hand-access device to allow the surgical procedure to be converted from an open procedure into a hand-assisted laparoscopic procedure; an instrument port far the insertion of instruments; a trocar for use in laparoscopic surgery, an internal organ retractor to assist in the displacement of internal structures from the operative field; or an illuminating means to deliver illumination to an area shaded from the theatre lights. It will be clear to those skilled in the art that the enhancements are not limited to the brief list mentioned here.

The wound retractor may be constructed in other annular shapes. For example the distal and proximal rings attached to the elastomeric sleeve may be oval or elliptical instead of circular.

The retractor may be used to retract and protect the margins of a natural bodily orifice such as the anus or vagina, or can be used to retract and protect the edges of a man-made stoma such as is created for tracheostomy or following gastrointestinal surgery.

The invention is not limited to the embodiments hereinbefore described which may be varied in both construction and detail.

What is claimed is:

1. A surgical wound retractor comprising:
    a distal 105 anchoring member for insertion into a wound opening;
    a connecting 106 means having an inner wound engaging portion and an outer portion, the wound engaging portion being mounted to the distal anchoring member, the connecting means having an insertion configuration in which the inner wound engaging portion has a reduced radial dimension and a retracting configuration;
    an external guide 110 means for the outer portion of the connecting means;
    the external guide means being movable relative to the connecting means to shorten the axial extent of the connecting means and thereby bias the wound engaging portion of the connecting member into the retracting configuration to retract the wound opening laterally; and
    external 120 anchoring means for anchoring the connecting means to maintain retraction of the opening.

2. A retractor as claimed in claim 1 wherein at least the inner wound engaging portion of the connecting means comprises a sleeve for extending around the wound opening to protect the opening.

3. A retractor as claimed in claim 1 wherein the outer portion of the connecting means comprises a sleeve extension of the inner wound engaging portion of the connecting means.

4. A retractor as claimed in claim 1 wherein the connecting means comprises a generally cylindrical sleeve.

5. A retractor as claimed in claim 1 wherein the guide means comprises an annular ring means.

6. A retractor as claimed in claim 5 wherein the annular ring means comprises inner and outer ring parts between which the connecting means is led.

7. A retractor as claimed in claim 6 wherein the outer ring part includes the anchor means for anchoring the connecting means.

8. A retractor as claimed in claim 7 wherein the anchor means comprises anchor formations on the outer ring to which the connecting means is attached on retraction of the opening.

9. A retractor as claimed in claim 6 wherein the inner ring means defines a projection for location in a complementary recess of the outer ring with the connecting means located therebetween.

10. A retractor as claimed in claim 6 wherein the inner-ring is a relatively loose fit in the recess of the outer ring part.

11. A retractor as claimed in claim 6 wherein at least a portion of one of the ring parts is movable from a rest position in which the connecting member is substantially clamped between the ring parts to a release position in which at least a portion of the connecting member is movable relative to the ring parts.

12. A retractor as claimed in claim 11 wherein only a portion of the connecting member is movable relative to the ring parts in the release position.

13. A retractor as claimed in claim 6 wherein the inner ring is a relatively tight fit in the outer ring part to grip the connecting member therebetween.

14. A retractor as claimed in claim 6 wherein the outer ring part comprises plurality of interconnected segments which are independently movable to facilitate localised release of the connecting member for adjusting of the retraction force applied at the opening.

15. A retractor as claimed in claim 14 wherein the outer ring part or segment thereof is manually manipulable between a interconnected segments clamped rest position and the release position.

16. A retractor as claimed in claim 1 wherein the connecting means includes a proximal reinforcing means for engagement with the external anchoring means.

17. A retractor as claimed in claim 16 wherein the proximal reinforcing means is a proximal ring.

18. A retractor as claimed in claim 1 wherein the distal anchoring means is of resilient material.

19. A retractor as claimed in claim 1 wherein the distal anchoring means is an O-ring.

20. A retractor as claimed in claim 1 wherein at least an outer surface of the guide means which engages with the connecting means is of a material with a low coefficient of friction.

21. A retractor as claimed in claim 20 wherein at least an outer surface of the guide means is of polytetrafluroethylene.

22. A retractor as claimed in claim 1 including a platform for attachment of another device to the retractor.

23. A retractor as claimed in claim 6 wherein one of the ring part defines a platform for attachment of another device to the retractor.

24. A method for retracting a wound opening using a surgical wound retractor comprising a distal anchoring member, a connecting means having a wound engaging portion mounted to the distal anchoring member and an outer portion, an external guide means for the outer portion of the connecting means and an external anchoring means; the method comprising the steps of:

positioning the distal anchoring member to be retained inside a wound opening with the connecting means extending outwardly; therefrom through the opening, moving the external guide means relative to the outer portion of the connecting means to shorten the axial extent of the connecting means and thereby bias the wound engaging portion into a retracting configuration to retract the wound opening; and anchoring the connecting means to maintain retraction of the wound opening.

25. A method as claimed in claim 24 including the steps of moving the external guide means relative to the outer portion of the connecting means to partially retract the wound opening, gripping the outer portion of the connecting means and pulling it relative to the guide means to fully retract the wound opening.

26. A method as claimed in claim 25 including the steps of:

(a) gripping a local section of the outer portion of the connecting means while the remaining section of the outer portion of the connecting means is anchored, (b) pulling the local section to increase the retraction at a local area of the wound opening, and (c) anchoring the local section of the connecting means.

27. A method as claimed in claim 26 including repeating steps (a) to (c) for other local sections of the outer portion of the connecting means.

* * * * *